United States Patent
Bente, IV et al.

(10) Patent No.: US 10,251,996 B2
(45) Date of Patent: Apr. 9, 2019

(54) VARIABLE RATE CONTROLLED DELIVERY DRIVE MECHANISMS FOR DRUG DELIVERY PUMPS

(71) Applicant: UNL Holdings LLC, New York, NY (US)

(72) Inventors: Paul F. Bente, IV, Wayne, PA (US);
Ian B. Hanson, Wayne, PA (US);
Vincent E. Mandes, Willow Grove, PA (US); Sean M. O'Connor, West Chester, PA (US)

(73) Assignee: UNL Holdings LLC, New York, NY (US)

( * ) Notice: Subject to any disclaimer, the term of this patent is extended or adjusted under 35 U.S.C. 154(b) by 538 days.

(21) Appl. No.: 14/423,565

(22) PCT Filed: Aug. 29, 2013

(86) PCT No.: PCT/US2013/057327
§ 371 (c)(1),
(2) Date: Feb. 24, 2015

(87) PCT Pub. No.: WO2014/036285
PCT Pub. Date: Mar. 6, 2014

(65) Prior Publication Data
US 2015/0217045 A1    Aug. 6, 2015

Related U.S. Application Data

(60) Provisional application No. 61/694,534, filed on Aug. 29, 2012, provisional application No. 61/731,744, (Continued)

(51) Int. Cl.
*A61M 5/145* (2006.01)
*A61M 5/168* (2006.01)
*A61M 5/142* (2006.01)

(52) U.S. Cl.
CPC ........ *A61M 5/1454* (2013.01); *A61M 5/1452* (2013.01); *A61M 5/14546* (2013.01);
(Continued)

(58) Field of Classification Search
CPC .......... A61M 2005/14208; A61M 2202/0007; A61M 2205/3334; A61M 5/1452;
(Continued)

(56) References Cited

U.S. PATENT DOCUMENTS 1,929,774 A * 10/1933 Davis ...................... F16N 11/08
                                                        184/45.1
3,336,924 A     8/1967 Samoff et al.
(Continued)

FOREIGN PATENT DOCUMENTS

CN       101557847 A    10/2009
CN       101631585 A     1/2010
(Continued)

OTHER PUBLICATIONS

European Search Report for EP 17163810, "Variable Rate Controlled Delivery Drive Mechanisms for Drug Delivery Pumps", dated Jul. 18, 2017.
(Continued)

*Primary Examiner* — Quynh-Nhu H Vu
(74) *Attorney, Agent, or Firm* — Hamilton, Brook, Smith & Reynolds, P.C.

(57) ABSTRACT

A variable rate controlled delivery drive mechanism includes a drive mechanism housing, at least partially within which initially resides a biasing member positioned in an initially energized state within an inner cavity of a piston. The drive mechanism may include a gear drive having one or more screws and one or more corresponding nuts. The piston contacts a plunger seal and is configured to axially translate the plunger seal, by force asserted upon it from the
(Continued)

biasing member, from a first position to a second position within a drug container for drug delivery. The biasing member is metered from free expansion from its energized state by the gear drive and a gear assembly mechanism having a motor. A drug delivery pump utilizes such variable rate controlled delivery mechanisms. A status reader configured to recognize one or more corresponding status triggers is utilized to provide feedback to a user.

25 Claims, 10 Drawing Sheets

Related U.S. Application Data filed on Nov. 30, 2012, provisional application No. 61/748,667, filed on Jan. 3, 2013.

(52) U.S. Cl.
CPC .... *A61M 5/14566* (2013.01); *A61M 5/16804* (2013.01); *A61M 2005/14208* (2013.01); *A61M 2202/0007* (2013.01); *A61M 2205/3334* (2013.01)

(58) Field of Classification Search
CPC ............ A61M 5/1454; A61M 5/14546; A61M 5/14566; A61M 5/16804; A61M 2005/3152; A61M 5/31526; A61M 5/31528; A61M 5/31558; A61M 5/31575
See application file for complete search history.

(56) References Cited

U.S. PATENT DOCUMENTS

| | | | |
|---|---|---|---|
| 3,401,692 A | 9/1968 | Harris, Jr. | |
| 3,413,974 A | 12/1968 | Cohen | |
| 3,940,003 A | 2/1976 | Larson | |
| 4,004,586 A | 1/1977 | Christensen et al. | |
| 4,048,997 A | 9/1977 | Raghavachari et al. | |
| 4,565,543 A | 1/1986 | Bekkering et al. | |
| 4,668,220 A | 5/1987 | Hawrylenko | |
| 4,673,400 A | 6/1987 | Martin | |
| 4,685,903 A | 8/1987 | Cable et al. | |
| 4,755,172 A | 7/1988 | Baldwin | |
| 4,755,173 A | 7/1988 | Konopka et al. | |
| 4,840,620 A | 6/1989 | Kobayashi et al. | |
| 4,921,487 A | 5/1990 | Buffet et al. | |
| D326,611 S | 6/1992 | Dinand | |
| 5,147,311 A | 9/1992 | Pickhard | |
| 5,167,816 A | 12/1992 | Kruger et al. | |
| 5,271,528 A * | 12/1993 | Chien ................. F16N 11/08 184/38.4 |
| 5,747,350 A | 5/1998 | Sattler | |
| 5,779,677 A | 7/1998 | Frezza | |
| 5,795,339 A | 8/1998 | Erskine | |
| 5,800,405 A | 9/1998 | McPhee | |
| 5,851,197 A | 12/1998 | Marano et al. | |
| 5,858,001 A | 1/1999 | Tsals et al. | |
| 5,919,167 A | 7/1999 | Mulhauser et al. | |
| D430,289 S | 8/2000 | Mason et al. | |
| 6,159,161 A * | 12/2000 | Hodosh ................. A61M 5/20 600/561 |
| 6,248,093 B1 | 6/2001 | Moberg | |
| 6,368,314 B1 | 4/2002 | Kipfer et al. | |
| D457,949 S | 5/2002 | Krug et al. | |
| D461,241 S | 8/2002 | Moberg et al. | |
| 6,645,177 B1 | 11/2003 | Shearn | |
| 6,699,218 B2 | 3/2004 | Flaherty et al. | |
| 6,802,394 B2 * | 10/2004 | Patterson ................. F16N 11/04 184/105.1 |
| 7,036,684 B1 | 5/2006 | Hantman et al. | |
| 7,063,684 B2 | 6/2006 | Moberg | |
| 7,250,037 B2 | 7/2007 | Shermer et al. | |
| D564,087 S | 3/2008 | Yodfat et al. | |
| D585,543 S | 1/2009 | Yodfat et al. | |
| 7,479,135 B2 | 1/2009 | Richter et al. | |
| D586,463 S | 2/2009 | Evans et al. | |
| 7,611,503 B2 | 11/2009 | Spohn et al. | |
| 7,780,636 B2 | 8/2010 | Radmer et al. | |
| 7,803,134 B2 | 9/2010 | Sharifi et al. | |
| D629,503 S | 12/2010 | Caffey et al. | |
| 7,846,132 B2 | 12/2010 | Gravesen et al. | |
| 7,879,010 B2 | 2/2011 | Hunn et al. | |
| 7,905,859 B2 | 3/2011 | Bynum et al. | |
| 7,927,306 B2 | 4/2011 | Cross et al. | |
| 7,967,795 B1 | 6/2011 | Cabiri | |
| 8,029,472 B2 | 10/2011 | Leinsing et al. | |
| 8,048,031 B2 | 11/2011 | Shaw et al. | |
| 8,152,771 B2 | 4/2012 | Mogensen et al. | |
| 8,157,769 B2 | 4/2012 | Cabiri | |
| 8,162,892 B2 | 4/2012 | Mogensen et al. | |
| 8,167,844 B2 | 5/2012 | Dillard, III | |
| 8,187,232 B2 | 5/2012 | Chong et al. | |
| D669,165 S | 10/2012 | Estes et al. | |
| 8,308,687 B2 | 11/2012 | Carrel et al. | |
| 8,409,145 B2 | 4/2013 | Raymond et al. | |
| D684,685 S | 6/2013 | Schneider et al. | |
| D684,686 S | 6/2013 | Cronenberg | |
| D685,083 S | 6/2013 | Schneider et al. | |
| 8,591,465 B2 | 11/2013 | Hommann | |
| D709,183 S | 7/2014 | Kemlein | |
| 8,795,234 B2 | 8/2014 | Kadamus et al. | |
| 8,939,935 B2 | 1/2015 | O'Connor et al. | |
| D723,157 S | 2/2015 | Clemente et al. | |
| 9,005,169 B2 | 4/2015 | Gravesen et al. | |
| D745,142 S | 12/2015 | O'Connor et al. | |
| D752,442 S | 3/2016 | O'Donahue | |
| 9,387,289 B2 * | 7/2016 | Swan ................. A61M 5/1454 |
| D768,288 S | 10/2016 | O'Connor et al. | |
| 9,463,280 B2 | 10/2016 | Cabiri | |
| 9,707,335 B2 | 7/2017 | Agard et al. | |
| 9,814,832 B2 | 11/2017 | Agard et al. | |
| 9,999,727 B2 | 6/2018 | O'Connor et al. | |
| 2002/0123740 A1 | 9/2002 | Flaherty et al. | |
| 2003/0199816 A1 | 10/2003 | Ramming | |
| 2004/0039344 A1 | 2/2004 | Baldwin et al. | |
| 2004/0092878 A1 | 5/2004 | Flaherty | |
| 2005/0033232 A1 | 2/2005 | Kriesel | |
| 2007/0010789 A1 | 1/2007 | Peter et al. | |
| 2007/0059989 A1 | 3/2007 | Kura | |
| 2007/0073228 A1 | 3/2007 | Mernoe et al. | |
| 2007/0179444 A1 | 8/2007 | Causey et al. | |
| 2008/0132842 A1 | 6/2008 | Flaherty | |
| 2008/0269683 A1 | 10/2008 | Bikovsky | |
| 2008/0269687 A1 | 10/2008 | Chong et al. | |
| 2009/0048561 A1 | 2/2009 | Burren et al. | |
| 2009/0093792 A1 | 4/2009 | Gross et al. | |
| 2009/0124979 A1 | 5/2009 | Raymond et al. | |
| 2009/0145509 A1 | 6/2009 | Baker et al. | |
| 2009/0204077 A1 | 8/2009 | Hasted et al. | |
| 2009/0240240 A1 | 9/2009 | Hines et al. | |
| 2011/0098652 A1 | 4/2011 | Hasted et al. | |
| 2011/0160678 A1 | 6/2011 | Chong et al. | |
| 2011/0166509 A1 | 7/2011 | Gross et al. | |
| 2011/0270188 A1 | 11/2011 | Caffey et al. | |
| 2011/0301534 A1 | 12/2011 | Renz et al. | |
| 2012/0035546 A1 | 2/2012 | Cabiri | |
| 2012/0096953 A1 | 4/2012 | Bente, IV et al. | |
| 2012/0123354 A1 | 5/2012 | Woehr | |
| 2012/0136306 A1 * | 5/2012 | Bartha ................. A61M 5/30 604/154 |
| 2012/0172804 A1 | 7/2012 | Plumptre | |
| 2012/0211946 A1 | 8/2012 | Halili et al. | |
| 2013/0060196 A1 | 3/2013 | O'Connor et al. | |
| 2013/0066274 A1 | 3/2013 | O'Connor et al. | |
| 2013/0131595 A1 | 5/2013 | Ekman et al. | |
| 2013/0204195 A1 * | 8/2013 | Ekman ................. A61M 5/2033 604/197 |
| 2013/0253420 A1 | 9/2013 | Favreau | |
| 2014/0200510 A1 | 7/2014 | Agard et al. | |
| 2014/0207065 A1 | 7/2014 | Yavorsky | |
| 2014/0231427 A1 | 8/2014 | Botet | |

(56) References Cited

U.S. PATENT DOCUMENTS

| | | |
|---|---|---|
| 2015/0065988 A1 | 3/2015 | Holderle et al. |
| 2015/0141920 A1 | 5/2015 | O'Connor et al. |
| 2015/0209505 A1 | 7/2015 | Hanson et al. |
| 2015/0217045 A1 | 8/2015 | Bente, IV et al. |
| 2015/0297827 A1 | 10/2015 | Hanson et al. |
| 2017/0281859 A1 | 10/2017 | Agard et al. |
| 2018/0043091 A1 | 2/2018 | Agard et al. |

FOREIGN PATENT DOCUMENTS

| | | |
|---|---|---|
| CN | 102526833 A | 7/2012 |
| CN | 102665799 A | 9/2012 |
| CN | 104751392 A | 7/2015 |
| EP | 0589328 A2 | 3/1994 |
| EP | 1219283 A2 | 7/2002 |
| EP | 1702635 A2 | 9/2006 |
| EP | 1341569 B1 | 1/2007 |
| EP | 1427471 B1 | 2/2008 |
| EP | 1695727 B1 | 7/2008 |
| EP | 1513580 B1 | 3/2009 |
| EP | 2 077 128 A1 | 7/2009 |
| EP | 2269559 A2 | 1/2011 |
| EP | 2379134 A1 | 10/2011 |
| EP | 2429612 A1 | 3/2012 |
| EP | 2433663 A1 | 3/2012 |
| GB | 2166497 A | 5/1986 |
| GB | 2452286 A | 3/2009 |
| JP | 9-507416 A | 7/1997 |
| JP | 2002-524217 A | 8/2002 |
| JP | 2003-527159 A | 9/2003 |
| JP | 2004-195227 A | 7/2004 |
| JP | 2004-528939 A | 9/2004 |
| JP | 2007-509657 A | 4/2007 |
| JP | 2008-536599 A | 9/2008 |
| JP | 2008-229344 A | 10/2008 |
| JP | 2009-101217 A | 5/2009 |
| JP | 2009-531143 A | 9/2009 |
| JP | 2009-542334 A | 12/2009 |
| JP | 2010-501211 A | 1/2010 |
| JP | 2010-501281 A | 1/2010 |
| JP | 2010-527255 A | 8/2010 |
| JP | 2010-528810 A | 8/2010 |
| JP | 2010-531196 A | 9/2010 |
| JP | 2010-535039 A | 11/2010 |
| JP | 2010-538751 A | 12/2010 |
| JP | 2010-540156 A | 12/2010 |
| JP | 2011-45537 A | 3/2011 |
| JP | 2011-511689 A | 4/2011 |
| JP | 2012-516736 A | 7/2012 |
| JP | 2012-516738 A | 7/2012 |
| TW | 201102654 A1 | 1/2011 |
| TW | M404020 | 5/2011 |
| WO | 9519194 A1 | 7/1995 |
| WO | 1997034651 A1 | 9/1997 |
| WO | WO 1999/020327 A2 | 4/1999 |
| WO | WO 1999/048546 A1 | 9/1999 |
| WO | 0015292 A2 | 3/2000 |
| WO | 0130424 A1 | 5/2001 |
| WO | WO 2002/028455 A | 4/2002 |
| WO | WO 2003/024504 A2 | 3/2003 |
| WO | 03/057286 A1 | 7/2003 |
| WO | WO 2003/103763 A1 | 12/2003 |
| WO | 2004035116 A1 | 4/2004 |
| WO | WO 2004/062714 A1 | 7/2004 |
| WO | WO 2005/037350 A2 | 4/2005 |
| WO | 2005044344 A1 | 5/2005 |
| WO | 2006129196 A1 | 12/2006 |
| WO | 2007126851 A2 | 11/2007 |
| WO | WO 2007/128767 A1 | 11/2007 |
| WO | WO 2008/024808 A2 | 2/2008 |
| WO | 2008105954 A2 | 9/2008 |
| WO | 2008133702 A1 | 11/2008 |
| WO | WO 2008/142394 A1 | 11/2008 |
| WO | 2008153460 A1 | 12/2008 |
| WO | 2009101145 A1 | 8/2009 |
| WO | WO 2010/029054 A1 | 3/2010 |
| WO | WO 2010/077807 A1 | 7/2010 |
| WO | WO 2010/084113 A1 | 7/2010 |
| WO | WO 2010/085338 A1 | 7/2010 |
| WO | WO 2010/112376 A1 | 10/2010 |
| WO | WO 2010/112377 A1 | 10/2010 |
| WO | WO 2010/132196 A1 | 11/2010 |
| WO | 2010139672 A1 | 12/2010 |
| WO | WO 2011/006652 A1 | 1/2011 |
| WO | WO 2011/046950 A1 | 4/2011 |
| WO | WO 2011/090956 A2 | 7/2011 |
| WO | 2011101831 A2 | 8/2011 |
| WO | WO 2011/121023 A1 | 10/2011 |
| WO | 2011/146166 A1 | 11/2011 |
| WO | WO 2012/032411 A2 | 3/2012 |
| WO | 2012117252 A1 | 9/2012 |
| WO | WO 2012/131044 A1 | 10/2012 |
| WO | WO 2013/033421 A2 | 3/2013 |
| WO | WO 2013/033467 A2 | 3/2013 |
| WO | WO 2013/040032 A1 | 3/2013 |
| WO | WO 2013/153041 A2 | 10/2013 |
| WO | WO 2013/156224 A1 | 10/2013 |
| WO | 2014036285 A2 | 3/2014 |
| WO | 2014116987 A1 | 7/2014 |
| WO | WO 2014/116274 A1 | 7/2014 |
| WO | 2015084428 A1 | 6/2015 |

OTHER PUBLICATIONS

European Patent Office, International Search Report and Written Opinion from PCT/US2013/057327 (May 21, 2014) 8 pages.

European Patent Office, International Search Report and Written Opinion from PCT/US2013/057327 (May 26, 2014) 10 pages.

Meng, et al., "MEMS-enabled implantable drug infusion pumps for laboratory animal research, preclinical, and clinical applications," Adv. Drug. Deliv. Rev., 64(14), Nov. 2012, pp. 1628-1638.

U.S. Food and Drug Administration, "Infusion Pump Improvement Initiative," Apr. 2010, pp. 1-6.

International Search Report and Written Opinion of the International Searching Authority for International Application No. PCT/US2012/053241, entitled: "Drive Mechanism for Drug Delivery Pumps With Integrated Status Indication," dated Feb. 28, 2013 (12 pgs).

International Search Report and Written Opinion of the International Searching Authority for International Application No. PCT/US2014/013005, entitled: "Drive Mechanism for Drug Delivery Pumps With Integrated Status Indication," dated May 22, 2014 (10 pgs).

* cited by examiner

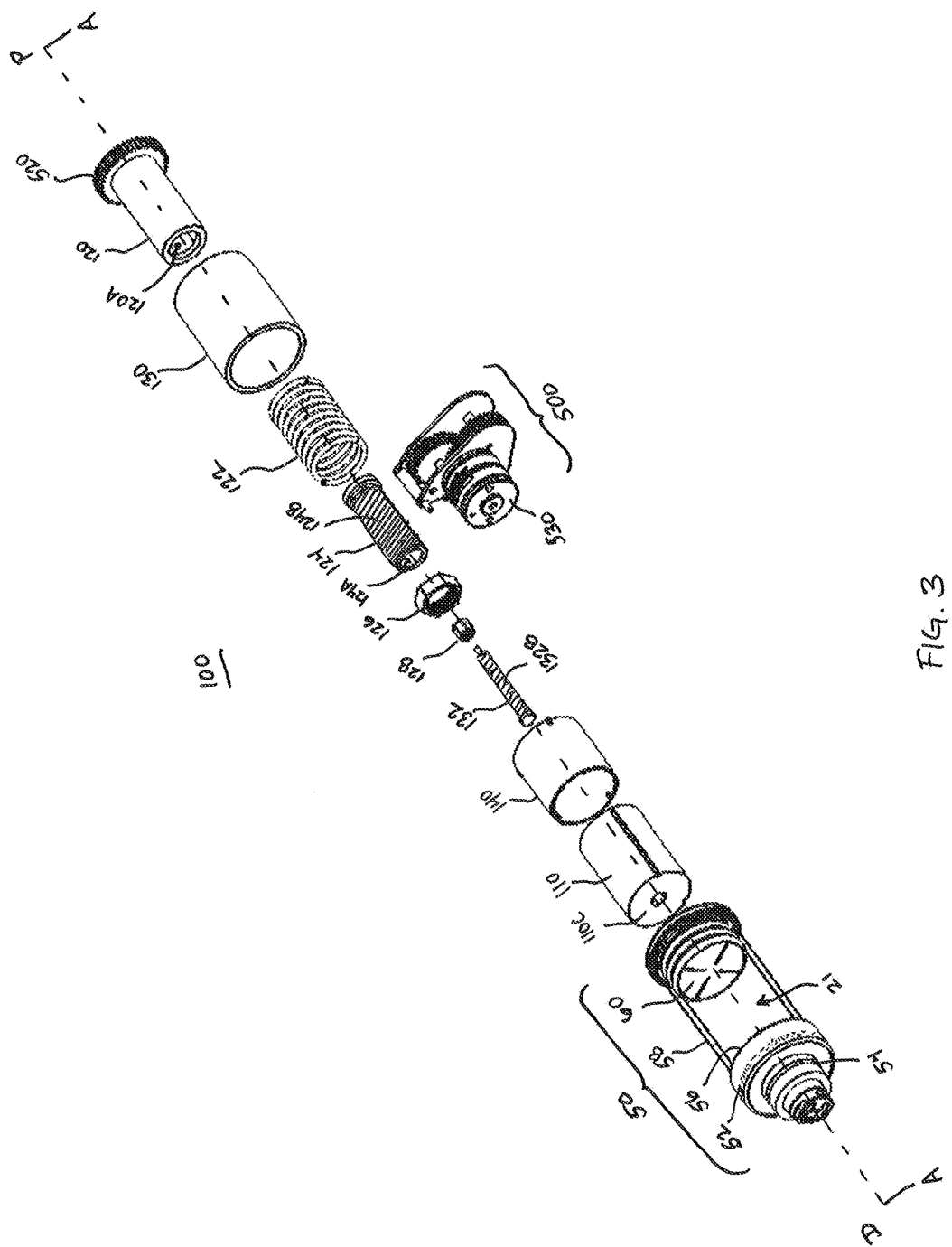

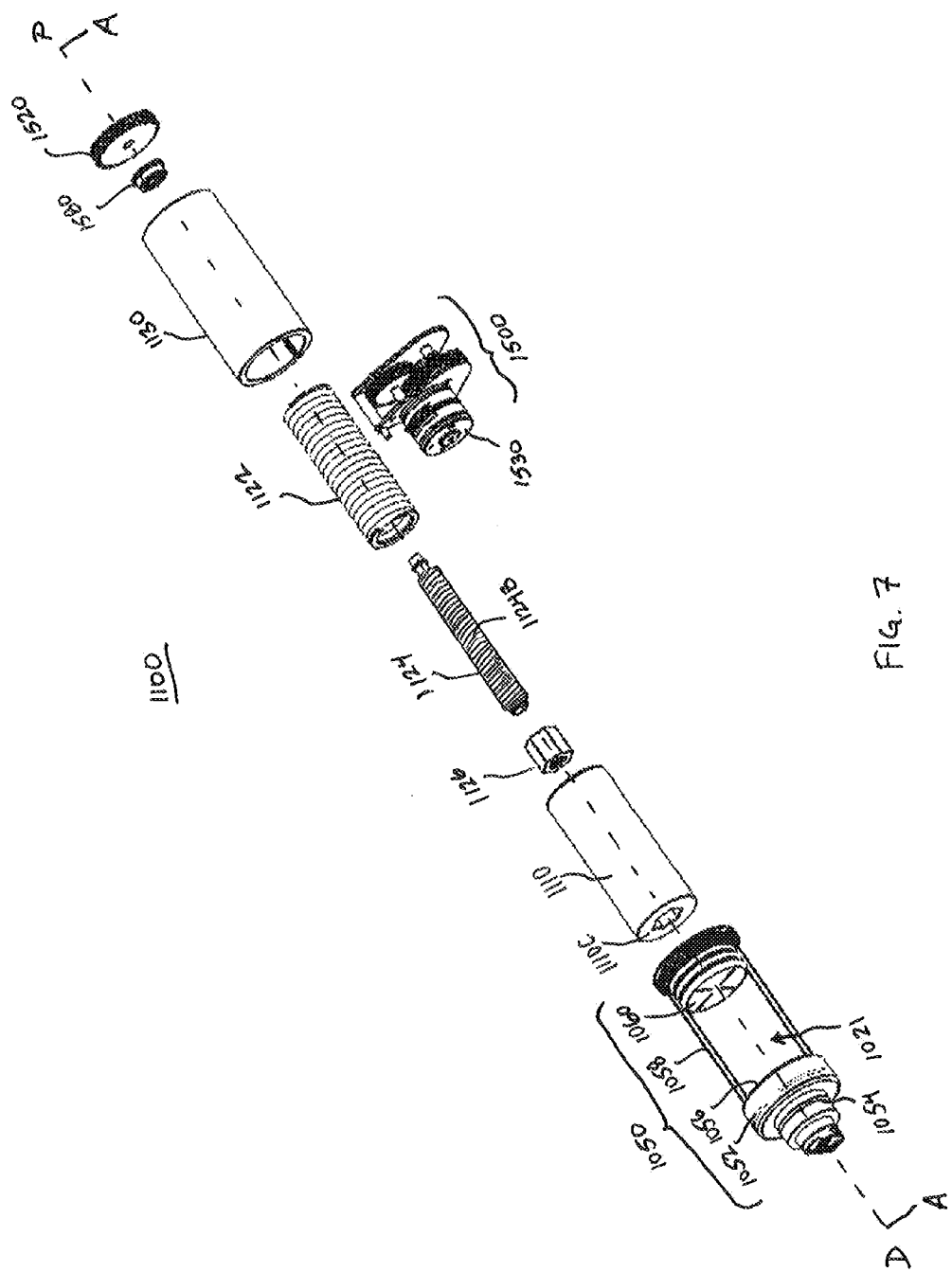

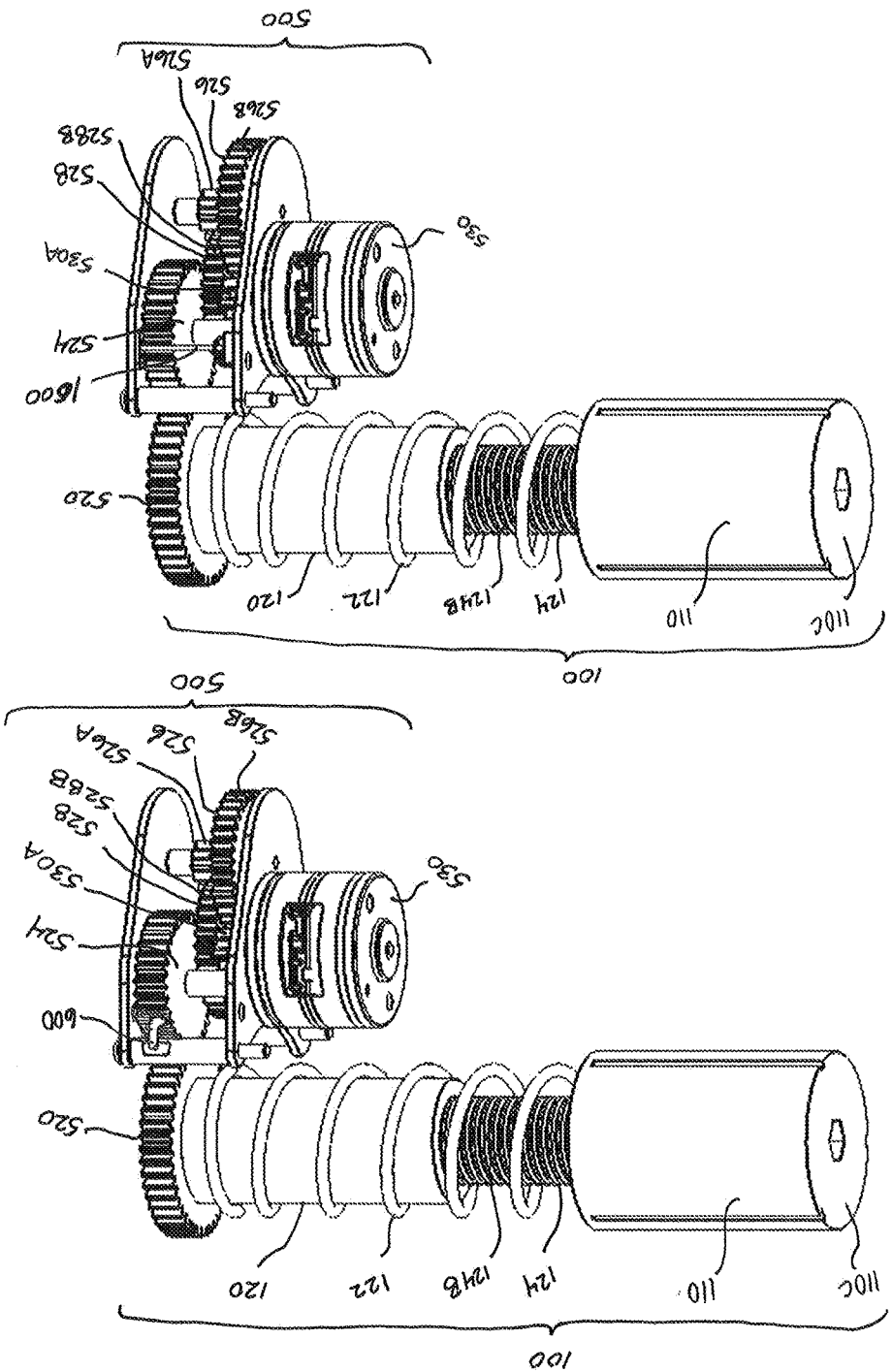

VARIABLE RATE CONTROLLED DELIVERY DRIVE MECHANISMS FOR DRUG DELIVERY PUMPS

CROSS-REFERENCE TO RELATED APPLICATIONS

This application claims priority to U.S. Provisional Application No. 61/694,534, filed on Aug. 29, 2012; U.S. Provisional Application No. 61/731,744, filed on Nov. 30, 2012; and U.S. Provisional Application No. 61/748,667, filed on Jan. 3, 2013 which are included by reference herein in their entirety for all purposes.

FIELD

THIS INVENTION relates to drug delivery pumps. More particularly, this invention relates to drive mechanisms for the variable rate controlled delivery of drug substances, drug delivery pumps with variable rate drive mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides drive mechanisms for the variable rate controlled delivery of drug substances, drug delivery pumps with variable rate drive mechanisms, the methods of operating such devices, and the methods of assembling such devices. Notably, the drive mechanisms of the present invention control the rate of drug delivery by metering, providing resistance, or otherwise preventing free axial translation of the plunger seal utilized to force a drug substance out of a drug container. The novel embodiments of the present invention thus are capable of delivering drug substances at variable rates. The variable rate drive mechanisms of the present invention may be pre-configurable or dynamically configurable, such as by control by the power and control system, to meet desired delivery rates or profiles, as explained in detail below. Additionally, the drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. Because the end-of-dose indication is related to the physical end of axial translation of one or more components of the drive mechanism, the drive mechanism and drug pump provide a true end-of-dose indication to the user. Through these mechanisms, confirmation of drug dose delivery can accurately be provided to the user or administrator. Accordingly, the novel devices of the present invention alleviate one or more of the problems associated with prior art devices, such as those referred to above.

In a first embodiment, the present invention provides a variable rate controlled delivery drive mechanism which includes a drive mechanism housing, at least partially within which initially resides a biasing member positioned in an initially energized state within an inner cavity of a piston. The drive mechanism may further includes a gear drive having a gear and a substantially axial internal pass-through; a first screw which at least partially resides within the axial internal pass-through, said first screw also having a substantially axial pass-through and an external first pitch wherein the external first pitch is configured to engage a first nut which also resides within the internal pass-through of the gear drive; a second nut configured to engage a second screw having an external second pitch, said second nut positioned within an axial post of a piston, said axial post and second nut positioned to reside at least partially within the axial pass-through of the first screw. The piston has an interface surface adjacent to a plunger seal and is configured to axially translate the plunger seal, by force asserted upon it from the biasing member, from a first position to a second position within a drug container for drug delivery. The biasing member is member is metered or otherwise restrained from free expansion from its energized state. The first nut may be rotationally constrained (i.e. keyed) to the gear drive, while the second nut is rotationally constrained to the piston.

In another embodiment, the present invention provides a variable rate controlled delivery drive mechanism having a drive mechanism housing, at least partially within which initially resides a biasing member positioned in an initially energized state within an inner cavity of a piston. A gear may be connected to the proximal end of a drive screw having an external pitch configured to engage a nut. The nut may be rotationally constrained (i.e., keyed) to the piston. The piston has an interface surface adjacent to a plunger seal and is configured to axially translate the plunger seal, by force asserted upon it from the biasing member, from a first position to a second position within a drug container for drug delivery. The biasing member is metered or otherwise restrained from free expansion from its energized state.

In at least one embodiment, the drive mechanism may further include a gear assembly mechanism having a motor, the gear assembly mechanism configured to engage a gear to meter the free expansion of the biasing member from its energized state. The gear assembly mechanism having a motor may further include a pinion extending from motor; one or more compound gears each having a first gear and a second gear; and a trigger gear; wherein the pinion contacts the one or more compound gears which contacts the trigger gear, and the trigger gear contacts a gear to relay motion to the drive mechanism. The metering of the biasing member by the motor controls the rate or profile of drug delivery to a user.

In a further embodiment, the drive mechanism includes a status reader configured to read or recognize one or more corresponding status triggers, wherein, during operation of the drive mechanism, interaction between the status reader and the status triggers transmits a signal to a power and control system to provide feedback to a user. The status reader may be, for example, an optical status reader and the corresponding status triggers are gear teeth of the trigger gear, a mechanical status reader and the corresponding status triggers are gear teeth of the trigger gear, a mechanical status reader and the corresponding status triggers are external features of the piston and/or sleeve an optional sleeve, or an optical status reader and the corresponding status triggers are external features of the piston and/or an optional sleeve. The function of the gear assembly mechanism having a motor may be pre-programmed or dynamically controlled by a power and control system to meet a desired drug delivery rate or profile.

In yet another embodiment, the present invention provides a drug delivery pump with a variable rate controlled delivery mechanism. The drive mechanism may be as described above. In at least one embodiment, the drug pump may further include a gear assembly mechanism having a motor, the gear assembly mechanism configured to engage a gear to meter the free expansion of the biasing member from its energized state. The gear assembly mechanism having a motor may further include a pinion extending from motor; one or more compound gears each having a first gear and a second gear; and a trigger gear; wherein the pinion contacts the one or more compound gears which contacts the trigger gear, and the trigger gear contacts a gear to relay motion to the drive mechanism. The metering of the biasing member by the motor controls the rate or profile of drug delivery to a user.

In a further embodiment, the drug pump includes a status reader configured to read or recognize one or more corresponding status triggers, wherein, during operation of the drive mechanism, interaction between the status reader and the status triggers transmits a signal to a power and control system to provide feedback to a user. The status reader may be, for example, an optical status reader and the corresponding status triggers are gear teeth of the trigger gear, a mechanical status reader and the corresponding status triggers are gear teeth of the trigger gear, a mechanical status reader and the corresponding status triggers are external features of the piston and/or sleeve an optional sleeve, or an optical status reader and the corresponding status triggers are external features of the piston and/or an optional sleeve. The function of the gear assembly mechanism having a motor may be pre-programmed or dynamically controlled by a power and control system to meet a desired drug delivery rate or profile.

The novel embodiments of the present invention provide drive mechanisms which are capable of metering, providing resistance, or otherwise preventing free axial translation of the plunger seal utilized to force a drug substance out of a drug container and, thereby, controlling the rate of delivery of drug substances. The novel control delivery drive mechanisms are additionally capable of providing the incremental status of the drug delivery before, during, and after operation of the device. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. For example, the embodiments may include one or more batteries utilized to power the motor, drive mechanisms, and drug pumps of the present invention. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 3 shows an exploded view, along an axis "A," of the drive mechanism shown in FIG. 2;

FIG. 7 shows an exploded view, along an axis "A," of the drive mechanism shown in FIG. 6;

FIG. 10A shows an isometric view of a variable rate controlled delivery drive mechanism which incorporates a mechanical status indicator, according to a further embodiment of the present invention;

FIG. 10B shows an isometric view of a variable rate controlled delivery drive mechanism which incorporates an optical status indicator, according to yet another embodiment of the present invention.

DETAILED DESCRIPTION

Figure 1A:
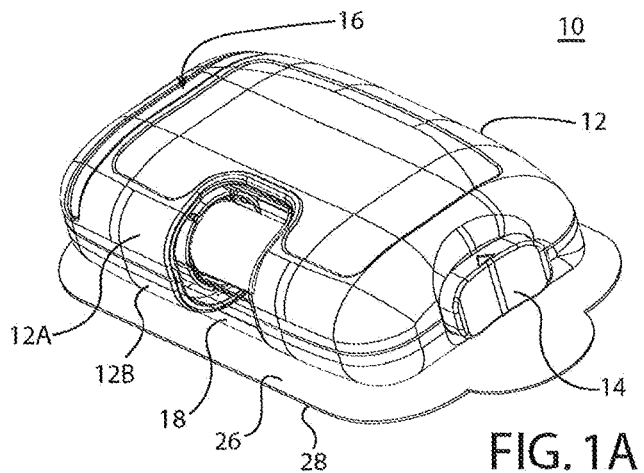
FIG. 1A shows an isometric view of a drug delivery pump having a variable rate controlled delivery drive mechanism, according to one embodiment of the present invention.

The present invention provides variable rate drive mechanisms for the controlled delivery of drug substances and drug delivery pumps which incorporate such variable rate drive mechanisms. The variable rate drive mechanisms of the present invention control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the variable rate drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the variable rate drive mechanism and drug pump may provide an end-of-dose indication.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to crosslinked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of the drug pumps. According to various aspects and embodiments described herein, reference is made to a "biasing member", such as in the context of one or more biasing members for asserting force on a plunger seal. It will be appreciated that the biasing member may be any member that is capable of storing and releasing energy. Non-limiting examples include a spring, such as for example a coiled spring, a compression or extension spring, a torsional spring, or a leaf spring, a resiliently compressible or elastic band, or any other member with similar functions. In at least one embodiment of the present invention, the biasing member is a spring, preferably a compression spring.

The novel devices of the present invention provide variable rate controlled delivery drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pumps, drive mechanisms, and their respective components are described further herein with reference to the accompanying figures.

Figure 1B:
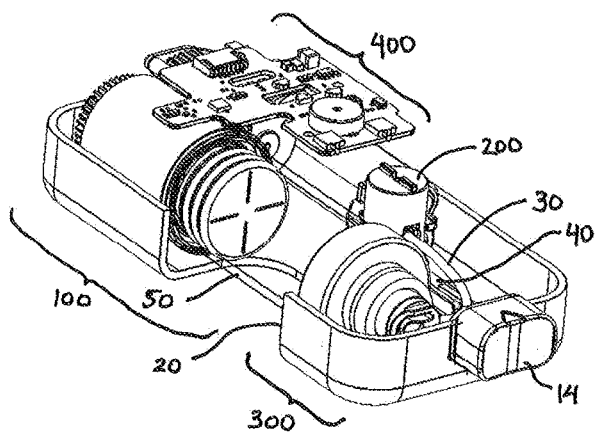
FIG. 1B shows an isometric view of the interior components of the drug delivery pump shown in FIG. 1A (shown without the adhesive patch)
Figure 1C:
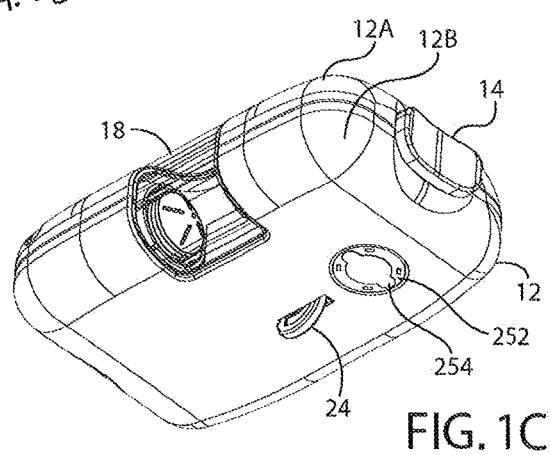
FIG. 1C shows an isometric view of the bottom of the drug delivery pump shown in FIG. 1A (shown without the adhesive patch)

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device or drug pump according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes assembly platform 20, sterile fluid conduit 30, drive mechanism 100 having drug container 50, insertion mechanism 200, fluid pathway connection 300, and power and control system 400. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12 is described in further detail hereinafter with reference to other components and embodiments of the present invention.

Drug pump is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 1C) may be provided in one embodiment as a safety feature to ensure that the power and control system 400, or the activation mechanism, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

The power and control system 400 may additionally be configured to accept various inputs from the user to dynamically control the drive mechanisms 100 to meet a desired drug delivery rate or profile. For example, the power and control system 400 may receive inputs, such as from partial or full activation, depression, and/or release of the activation mechanism 14, to set, initiate, stop, or otherwise adjust the control of the drive mechanism 100 via the power and control system 400 to meet the desired drug delivery rate or profile. Similarly, the power and control system 400 may be configured to receive such inputs to adjust the drug dose volume; to prime the drive mechanism, fluid pathway connection, and fluid conduit; and/or to start, stop, or pause operation of the drive mechanism 100. Such inputs may be received by the user directly acting on the drug pump 10, such as by use of the activation mechanism 14 or a different control interface, or the system 400 may be configured to receive such inputs from a remote device. Additionally or alternatively, such inputs may be pre-programmed.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Fluid Pathway Connection:

A number of fluid pathway connections may be utilized within the embodiments of the present invention. Generally, a suitable fluid pathway connection includes a sterile fluid conduit, a piercing member, and a sterile sleeve attached to a drug container or a sliding pierceable seal integrated within a drug container. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In one such embodiment, the fluid pathway connection may be substantially similar to that described in International Patent Application No. PCT/US2012/054861, which is included by reference herein in its entirety for all purposes. According to such an embodiment, the connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

Alternatively, the fluid pathway connection may be integrated into a drug container as described in International Patent Application No. PCT/US2013/030478, for example, which is included by reference herein in its entirety for all purposes. According to such an embodiment, a drug container may have a drug chamber within a barrel between a pierceable seal and a plunger seal. A drug fluid is contained in the drug chamber. Upon activation of the device by the user, a drive mechanism asserts a force on a plunger seal contained in the drug container. As the plunger seal asserts a force on the drug fluid and any air/gas gap or bubble, a combination of pneumatic and hydraulic pressure builds by compression of the air/gas and drug fluid and the force is relayed to the sliding pierceable seal. The sliding pierceable seal is caused to slide towards the cap, causing it to be pierced by the piercing member retained within the integrated sterile fluid pathway connection. Accordingly, the integrated sterile fluid pathway connection is connected (i.e., the fluid pathway is opened) by the combination pneumatic/hydraulic force of the air/gas and drug fluid within the drug chamber created by activation of a drive mechanism. Once the integrated sterile fluid pathway connection is connected or opened, drug fluid is permitted to flow from the drug container, through the integrated sterile fluid pathway connection, sterile fluid conduit, and insertion mechanism, and into the body of the user for drug delivery. In at least one embodiment, the fluid flows through only a manifold and a cannula and/or needle of the insertion mechanism, thereby maintaining the sterility of the fluid pathway before and during drug delivery.

Regardless of the fluid pathway connection utilized by the drug pump, the drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Insertion Mechanism:

A number of insertion mechanisms may be utilized within the drug pumps of the present invention. The pump-type delivery devices of the present invention may be connected in fluid flow communication to a patient or user, for example, through any suitable hollow tubing. A solid bore needle may be used to pierce the skin of the patient and place a hollow cannula at the appropriate delivery position, with the solid bore needle being removed or retracted prior to drug delivery to the patient. As stated above, the fluid can be introduced into the body through any number of means, including but not limited to: an automatically inserted needle, cannula, micro-needle array, or infusion set tubing. A number of mechanisms may also be employed to activate the needle insertion into the patient. For example, a biasing member such as a spring may be employed to provide sufficient force to cause the needle and cannula to pierce the skin of the patient. The same spring, an additional spring, or another similar mechanism may be utilized to retract the needle from the patient. In a preferred embodiment, the insertion mechanism may generally be as described in International Patent Application No. PCT/US2012/53174, which is included by reference herein in its entirety for all purposes. Such a configuration may be utilized for insertion of the drug delivery pathway into, or below, the skin (or muscle) of the patient in a manner that minimizes pain to the patient. Other known methods for insertion of a fluid pathway may be utilized and are contemplated within the bounds of the present invention.

In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the body of the user. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit 30 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 254 (shown in FIG. 1C).

According to at least one embodiment of the present invention, the insertion mechanism is initially locked into a ready-to-use stage by lockout pin(s) which are initially positioned within lockout windows of the insertion mechanism housing. In this initial configuration, insertion biasing member and retraction biasing member are each retained in their compressed, energized states. As shown in FIG. 1B, the lockout pin(s) 208 may be directly displaced by user depression of the activation mechanism 14. As the user disengages any safety mechanisms, such as an optional on-body sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows 202A of insertion mechanism housing 202. Displacement of the lockout pin(s) 208 permits insertion biasing member to decompress from its initial compressed, energized state. This decompression of the insertion biasing member drives the needle and the cannula into the body of the user. At the end of the insertion stage, the refraction biasing member is permitted to expand in the proximal direction from its initial energized state. This axial expansion in the proximal direction of the refraction biasing member refracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

Figure 2:
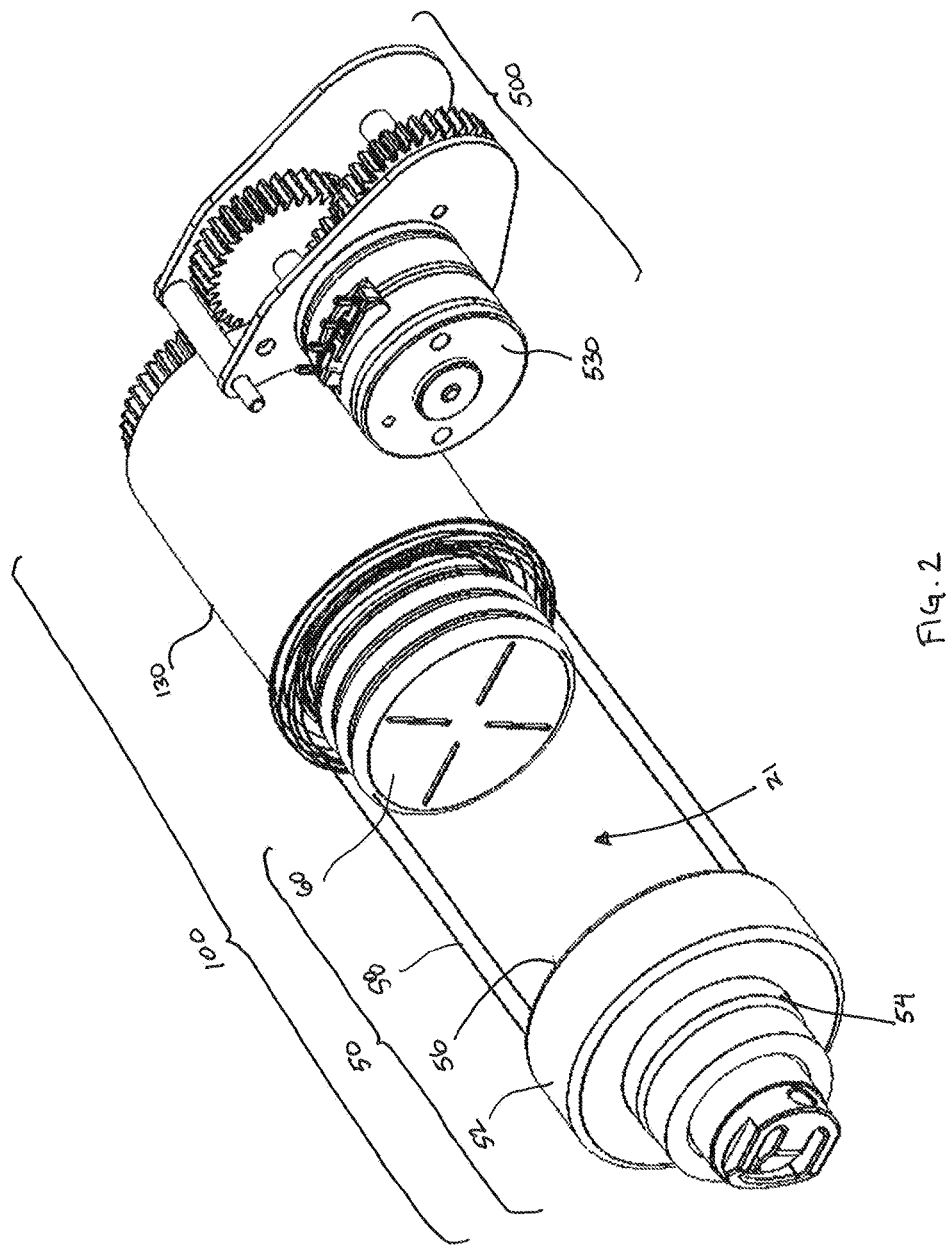
FIG. 2 shows an isometric view of a variable rate controlled delivery drive mechanism, according to at least one embodiment of the present invention.
Figure 4A:
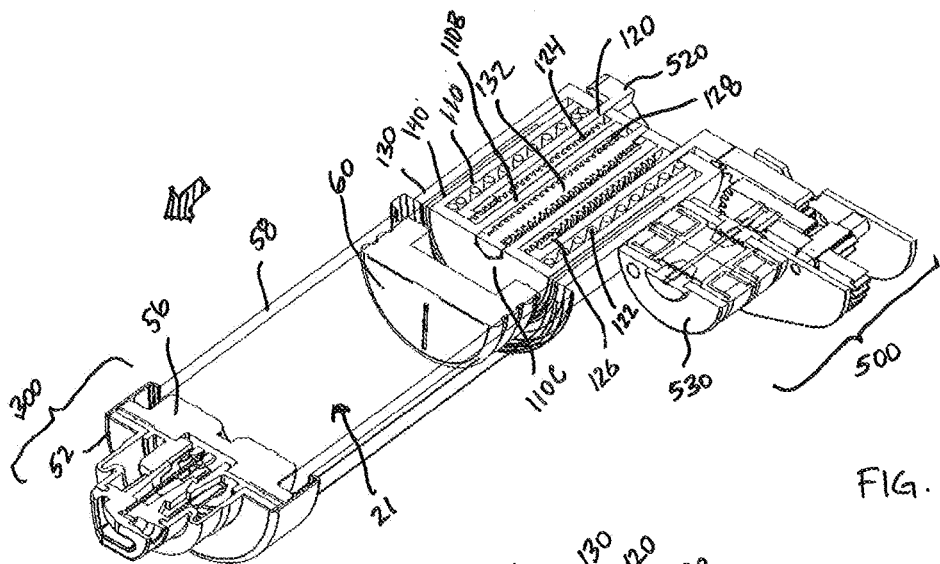
FIG. 4A shows an isometric cross-sectional view of the drive mechanism shown in FIG. 2 in an initial inactive state.
Figure 4B:
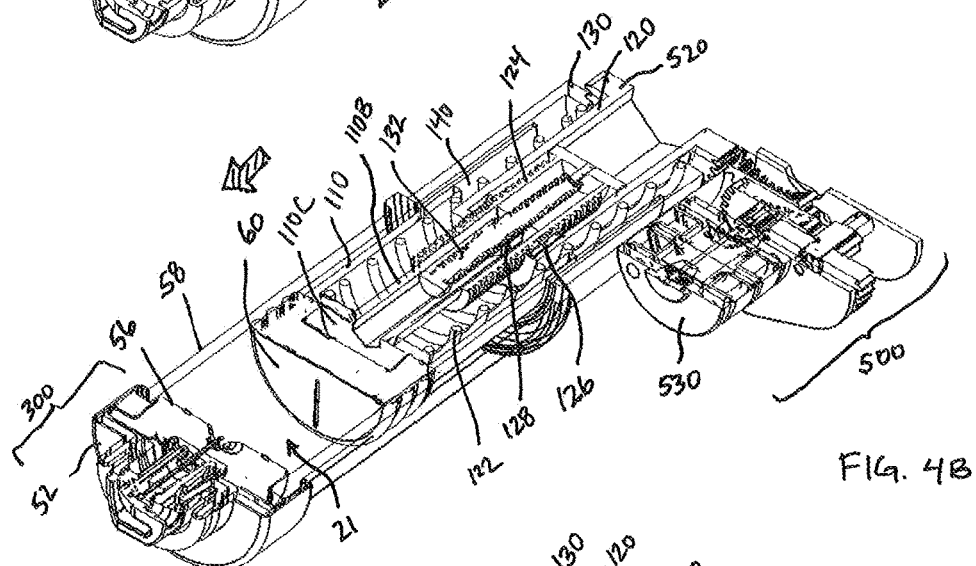
FIG. 4B shows an isometric cross-sectional view of the drive mechanism shown in FIG. 2 in an actuated state as the mechanism controls the rate or profile of drug delivery.
Figure 4C:
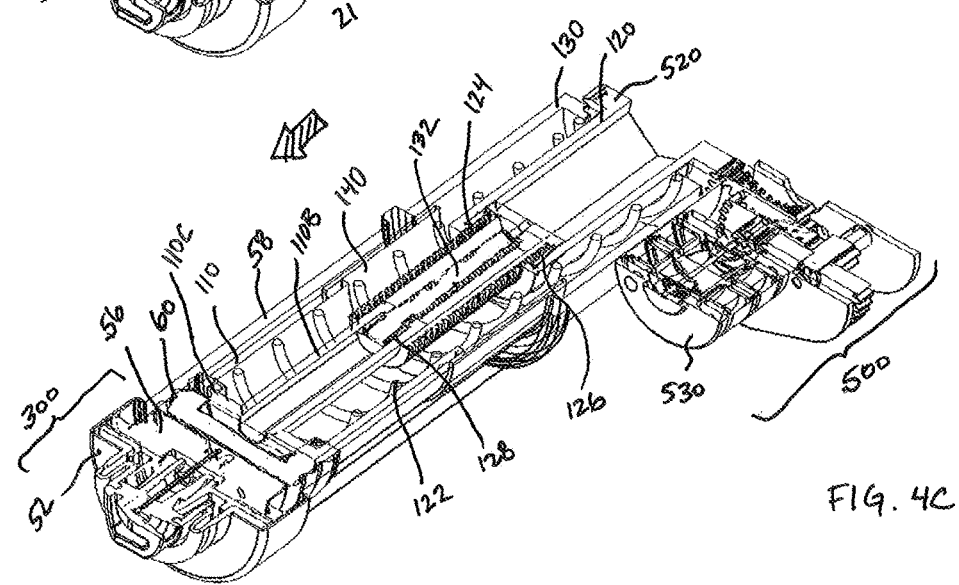
FIG. 4C shows an isometric cross-section view of the drive mechanism shown in FIG. 2 as the mechanism completes drug delivery.
Figure 5A:
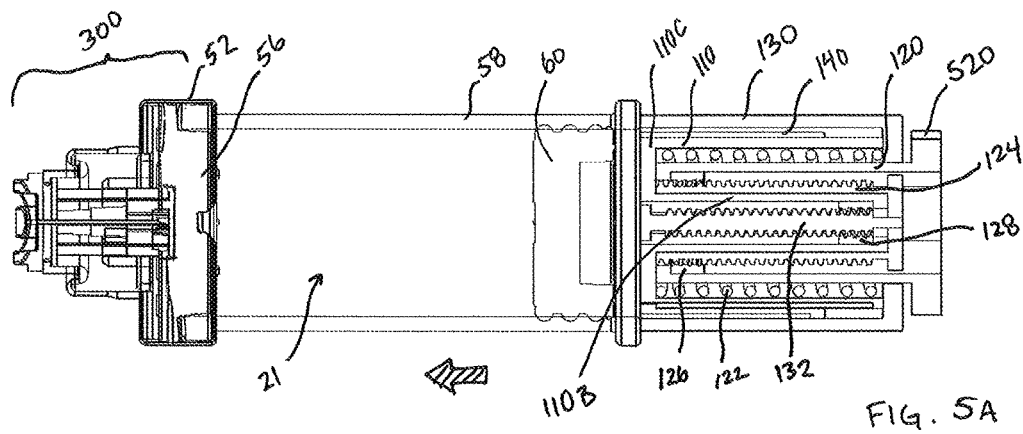
FIG. 5A shows a cross-sectional view of the drive mechanism shown in FIG. 4A in an initial inactive state.
Figure 5B:
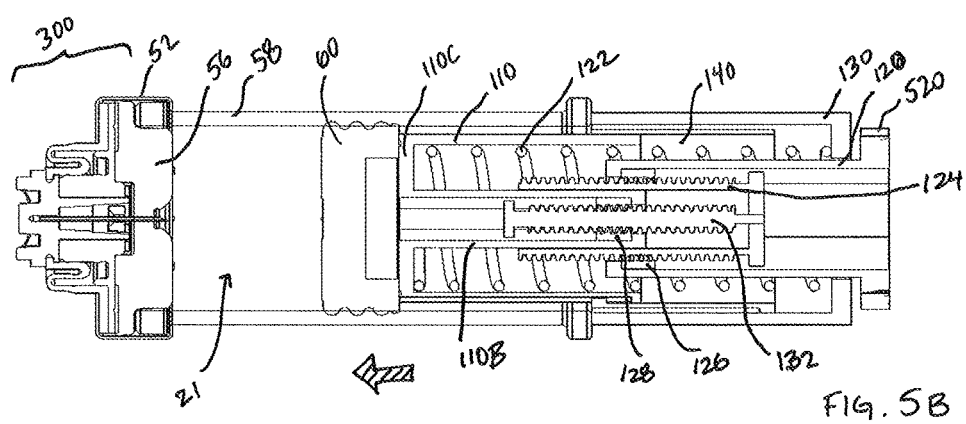
FIG. 5B shows a cross-sectional view of the drive mechanism shown in FIG. 4B in an actuated state as the mechanism controls the rate or profile of drug delivery.
Figure 5C:
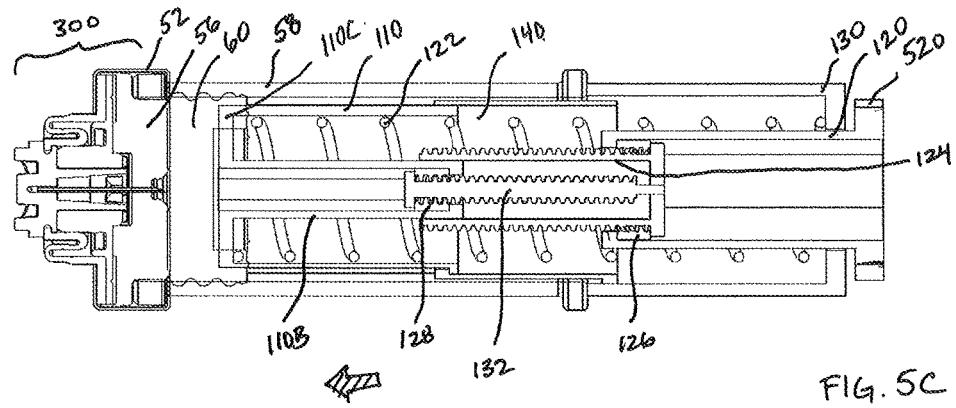
FIG. 5C shows a cross-sectional view of the drive mechanism shown in FIG. 4C as the mechanism completes drug delivery and, optionally, performs a compliance push to ensure completion of drug delivery.

Drive Mechanism:

With reference to the embodiments shown in FIGS. 2 and 3, drive mechanism 100 includes a drive housing 130, and a drug container 50 having a cap 52, a pierceable seal 56, a barrel 58, and a plunger seal 60. A drug chamber 21, located within the barrel 58 between the pierceable seal and the plunger seal 60, may contain a drug fluid for delivery through the insertion mechanism and drug pump into the body of the user. The seals described herein may be comprised of a number of materials but are, in a preferred embodiment, comprised of one or more elastomers or rubbers. The drive mechanism may further include a connection mount 54 to guide the insertion of the piercing member of the fluid pathway connection into the barrel 58 of the drug container 50. The drive mechanism 100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connection, for delivery through the fluid pathway connection, sterile fluid conduit, and insertion mechanism into the body of the user.

In one particular embodiment, the drive mechanism 100 employs one or more compression springs as the biasing member(s). Upon activation of the drug pump by the user, the power and control system may be actuated to directly or indirectly release the compression spring(s) from an energized state. Upon release, the compression spring(s) may bear against and act upon the plunger seal to force the fluid drug out of the drug container. The compression spring may bear against and act upon a piston which, in turn, acts upon the plunger seal to force the fluid drug out of the drug container. The fluid pathway connection may be connected through the pierceable seal prior to, concurrently with, or after activation of the drive mechanism to permit fluid flow from the drug container, through the fluid pathway connection, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Referring now to the embodiment of the drive mechanism shown in FIG. 2 and FIG. 3, the drive mechanism 100 includes a drug container 50 having a cap 52, a pierceable seal 56, a barrel 58, and a plunger seal 60, and optionally a connection mount 54. The drug container 50 is mounted to a distal end of a drive housing 130. Compressed within the drive housing 130, between the drug container 50 and the proximal end of the housing 130, are a drive biasing member 122 and a piston 110, wherein the drive biasing member 122 is configured to bear upon an interface surface 110C of the piston 110, as described further herein. Optionally, a cover sleeve 140 may be utilized to engage the piston 110 and cover the drive biasing member 122 to hide the biasing member 122 from user view upon expansion from its initial energized state. The cover sleeve 140 may be configured to engage and slide upon the piston 110, between the piston 110 and the distal end of the drive mechanism housing 130 to hide the biasing member 122 from user view upon expansion from its initial energized state.

As shown in FIG. 3, the variable rate controlled delivery drive mechanism 100 of the present invention may utilize a telescoping drive assembly which incorporates a gear drive 120 having a gear 520 and a substantially axial internal pass-through 120A, within which at least partially resides a first screw 124 having a substantially axial pass-through 124A and an external first pitch 124B. The external first pitch 124B is configured to engage and rotationally translate upon or within a first nut 126 which also resides within the internal pass-through 120A of the gear drive 120 (such as at the distal end of the internal pass-through 120A). Similarly, a second nut 128 resides within the axial pass-through 124A of the first screw 124 and is configured to engage and rotationally translate a second screw 132 having an external second pitch 132B. More accurately, the second nut 128 resides within an axial post 110B of the piston 110, which itself resides at least partially within the axial pass-through 124A of the first screw 124. The second nut 128 is configured to engage and rotationally translate upon or around the second screw 132 having the external second pitch 132B. These aspects are more clearly visible with reference to FIGS. 4A-4C and FIGS. 5A-5C. Because of this configuration of components, and because the axial rotation of the gear drive 120 indirectly causes axial translation of the piston 110, the variable rate controlled delivery drive mechanism shown in FIGS. 2, 3, 4A-4C and 5A-5C is referred to as a "telescoping" drive mechanism. The gear drive 120, notably, does not drive the delivery but only controls the delivery motion. The gear drive 120 controls the motion of the piston 110 and plunger seal 60, but does not apply the force necessary for drug delivery. Instead, the gear drive 120 merely meters or permits translation of the piston 110 and plunger seal 60 which are being driven to axially translate by the biasing member 122. Because the axial translation of the piston 110 and plunger seal 60 are driven by biasing member 122, and the gear drive 120 is merely metering or permitting axial translation, the force or power needed to meter the axial translation by the gear drive 120 is much smaller than that which would be required if the gear drive did drive the delivery. Accordingly, a smaller motor may be utilized by the embodiments of the present invention. The motor 530 may, accordingly, be selected from a variety of electromechanical sources capable of incremental motion, such as brushed DC motors, EC motors, stepper motors, solenoids, or other technologies that can produce controlled motion. In at least one embodiment, the motor 530 is most preferably a stepper motor.

Alternatively, a non-telescoping drive mechanism, as shown in FIGS. 6, 7, 8A-8C and 9A-9C may be utilized within the embodiments of the present invention. Referring now to the embodiment of the drive mechanism shown in FIG. 6 and FIG. 7, the drive mechanism 1100 includes a drug container 1050 having a cap 1052, a pierceable seal 1056, a barrel 1058, and a plunger seal 1060, and optionally a connection mount 1054. The drug container 1050 is mounted to a distal end of a drive housing 1130. Compressed within the drive housing 1130, between the drug container 1050 and the proximal end of the housing 1130, are a drive biasing member 1122 and a piston 1110, wherein the drive biasing member 1122 is configured to bear upon an interface surface 1110C of the piston 1110, as described further herein. As shown in FIG. 7, the variable rate controlled delivery drive mechanism 1100 of the present invention may utilize a non-telescoping drive assembly which incorporates a gear 1520 connected to the proximal end of a drive screw 1124 having an external pitch 1124B. The external pitch 1124B is configured to engage and rotationally translate upon or within a nut 1126. As the gear 1520 and drive screw 1124 are axially rotated, the threaded engagement between the drive screw 1124 and the nut 1126 permits axial translation of the piston 1110 by the biasing member 1122. These aspects are more clearly visible with reference to FIGS. 8A-8C and FIGS. 9A-9C. Because the axial rotation of the drive screw 1124 directly causes axial translation of the piston 1110, such embodiments of the present invention are referred to herein as "non-telescoping". As stated above with regard to the first embodiment, the drive screw 1124, notably, does not drive the delivery but only controls the delivery motion. The drive screw 1124 controls the motion of the piston 1110 and plunger seal 1060, but does not apply the force necessary for drug delivery. Instead, the drive screw 1124 merely meters or permits translation of the piston 1110 and plunger seal 1060 which are being driven to axially translate by the biasing member 1122. Because the axial translation of the piston 1110 and plunger seal 1060 are driven by biasing member 1122, and the drive screw 1124 is merely metering or permitting axial translation, the force or power needed to meter the axial translation by the drive screw 1124 is much smaller than that which would be required if the drive screw did drive the delivery. Accordingly, a smaller motor may be utilized by the embodiments of the present invention. The motor 1530 may, accordingly, be selected from a variety of electromechanical sources capable of incremental motion, such as brushed DC motors, EC motors, stepper motors, solenoids, or other technologies that can produce controlled motion. In at least one embodiment, the motor 1530 is most preferably a stepper motor.

FIGS. 4A-4C and FIGS. 5A-5C show the progression of the variable rate controlled delivery drive mechanism, according to the embodiment shown in FIGS. 2-3 having a telescoping drive mechanism configuration, as it progresses through activation, controlled delivery of a drug substance, and completion of drug delivery. As shown, a gear transmission assembly 500 having a motor 530 may be utilized to meter or otherwise prevent free axial translation of the biasing member 122 used to push a plunger seal 60 for the delivery of a drug substance out of drug chamber 21. The gear transmission assembly 500 is further detailed below with reference to FIGS. 10A-10B. Upon actuation of the variable rate controlled delivery drive mechanism 100 by the user, such as by activation of the power and control system, the motor 530 is caused to rotate the components of the gear transmission assembly 500 to correspondingly rotate gear 520. Substantially simultaneously or in advance of such activation of the motor 530, the biasing member 122 is unlocked or otherwise permitted to release from its initial energized state. The biasing member 122 is positioned within the drive mechanism housing 130 and held in an initial energized state between the drive mechanism housing 130 and the interior of the interface surface 110C of piston 110. Upon such unlocking or release the biasing member 122 will act upon and push the piston 110 (and the plunger seal 60 located substantially adjacent the piston 110 on the other side of the interface surface 110C) to drive the plunger seal 60 for drug delivery, if the biasing member 122 is unrestrained or not otherwise metered. The novel variable rate controlled delivery drive mechanisms of the present invention are configured to provide such restraint or metering on the expansion of the biasing member 122. Depending on a desired drug delivery rate or profile, as may be pre-programmed or dynamically controlled by the power and control system, the motor 530 of the gear assembly mechanism 500 may function to incrementally permit axial expansion of the biasing member 122 and, thus, axial translation of the piston 110 and plunger seal 60.

As the components of the gear assembly mechanism 500 are rotated by function of the motor 530 and corresponding gear interactions, gear 520 is caused to rotate. A gear drive 120 is connected to, or formed as part of, gear 520 such that axial rotation of the gear 520 causes axial rotation of the gear drive 120. Gear drive 520 has an internal pass-through 120 that is substantially axial, within which at least partially resides a first screw 124 having a substantially axial pass-through 124A and an external first pitch 124B. The external first pitch 124B is configured to engage and rotationally translate upon or within a first nut 126 which also resides within the internal pass-through 120A of the gear drive 120 (such as at the distal end of the internal pass-through 120A). The first nut 126 is rotationally keyed (i.e., constrained) or otherwise held in position (but permitted to axially translate) within the internal pass-through 120A of gear drive 120. As stated above, upon activation of the drive mechanism by the user, biasing member 122 will apply a force to piston 110 which is metered or restrained by the drive mechanism. As the gear drive 120 is caused to axially rotate, the keyed engagement of the first nut 126 with the gear drive 120 and the movable engagement between corresponding gear teeth of the first screw 124 (at the external first pitch 124B) with the first nut 126 permits axial translation of the first screw 124. Similarly, a second nut 128 resides within the axial pass-through 124A of the first screw 124 and is configured to engage and rotationally translate a second screw 132 having an external second pitch 132B. More accurately, the second nut 128 resides within an axial post 110B of the piston 110, which itself resides at least partially within the axial pass-through 124A of the first screw 124. The second nut 128 is configured to engage and rotationally translate upon or around the second screw 132 having the external second pitch 132B.

Accordingly, axial rotation (and translation) of the first screw 124 permits axial rotation and axial translation of the second screw 132. Accordingly, axial rotation of the gear 520 and gear drive 120 causes axial rotation and axial translation of the first screw 124. This is shown in the transition from FIG. 4A to FIG. 4B to FIG. 4C, and in the transition from FIG. 5A to FIG. 5B to FIG. 5C. Because the biasing member 122 is applying a force to piston 110, the metering by the components of the drive mechanism permits the biasing member 122 to axially translate the piston 110 and plunger seal 60 at variable rates or profiles for controlled drug delivery.

The variable rate controlled delivery drive mechanisms of the present invention can, of course, be configured such that both the first screw and second screw are caused to axially translate simultaneously, such as by manipulating the pitch ratio of the external first pitch 124B to the external second pitch 132B and their respective interactions with first nut 126 and second nut 128. As stated above, the gear drive 120 notably does not drive the delivery but only controls the delivery motion. The gear drive 120 controls the motion of the piston 110 and plunger seal 60, but does not apply the force necessary for drug delivery. Instead, the gear drive 120 merely meters or permits translation of the piston 110 and plunger seal 60 which are being driven to axially translate by the biasing member 122. Because the axial translation of the piston 110 and plunger seal 60 are driven by biasing member 122, and the gear drive 120 is merely metering or permitting axial translation, the force or power needed to meter the axial translation by the gear drive 120 is much smaller than that which would be required if the gear drive did drive the delivery. Optionally, a cover sleeve 140 may be utilized to hide the visibility of the biasing member 122 and other internal components from the user as the piston 110 is axially translated by the biasing member 122. The cover sleeve 140 may also assist in maintaining a rotationally fixed relationship between the non-rotating (relative to gear drive 120) components of the drive mechanism, including for example the drive mechanism housing 130 and the piston 110. This rotational constraint permits the screws and corresponding nuts to axially rotate, while the piston is permitted to axially translate. The embodiments shown in these figures utilize a telescoping drive mechanism configuration to obtain greater available axial translation while maintaining a smaller arrangement or dimensional footprint when in the compressed position.

Figure 6:
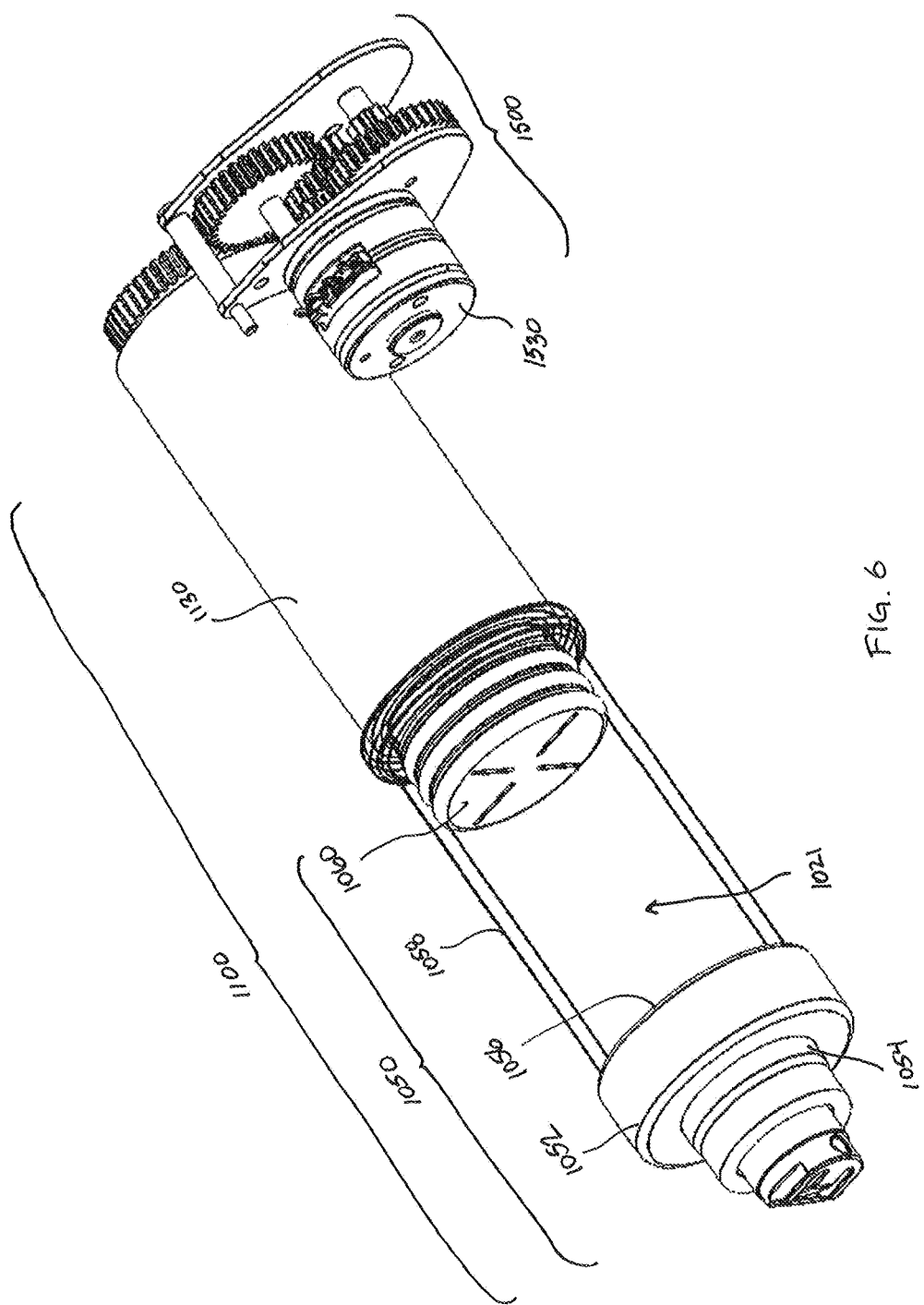
FIG. 6 shows an isometric view of a variable rate controlled delivery drive mechanism, according to another embodiment of the present invention.
Figure 8A:
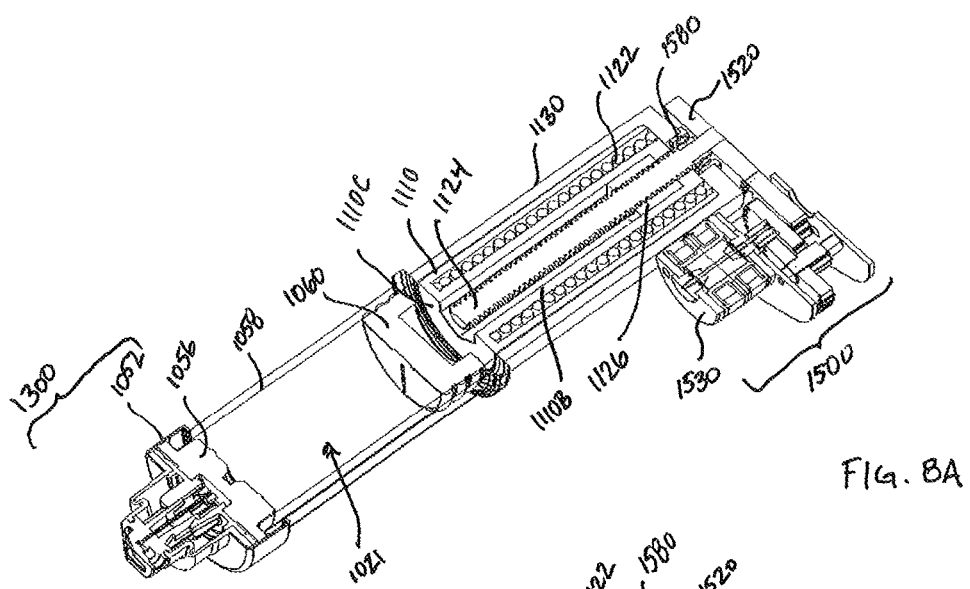
FIG. 8A shows an isometric cross-sectional view of the drive mechanism shown in FIG. 6 in an initial inactive state.
Figure 8B:
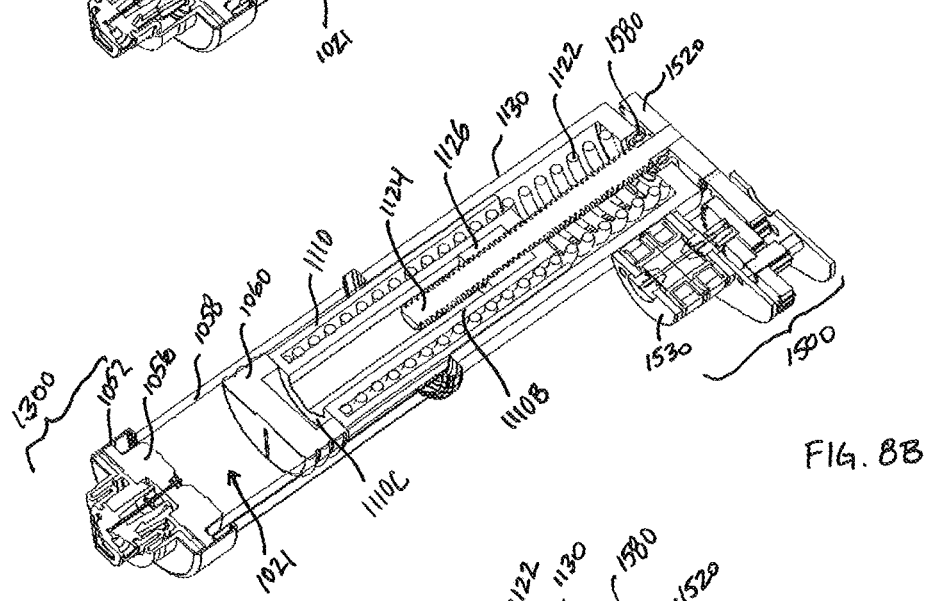
FIG. 8B shows an isometric cross-sectional view of the drive mechanism shown in FIG. 6 in an actuated state as the mechanism controls the rate or profile of drug delivery.
Figure 8C:
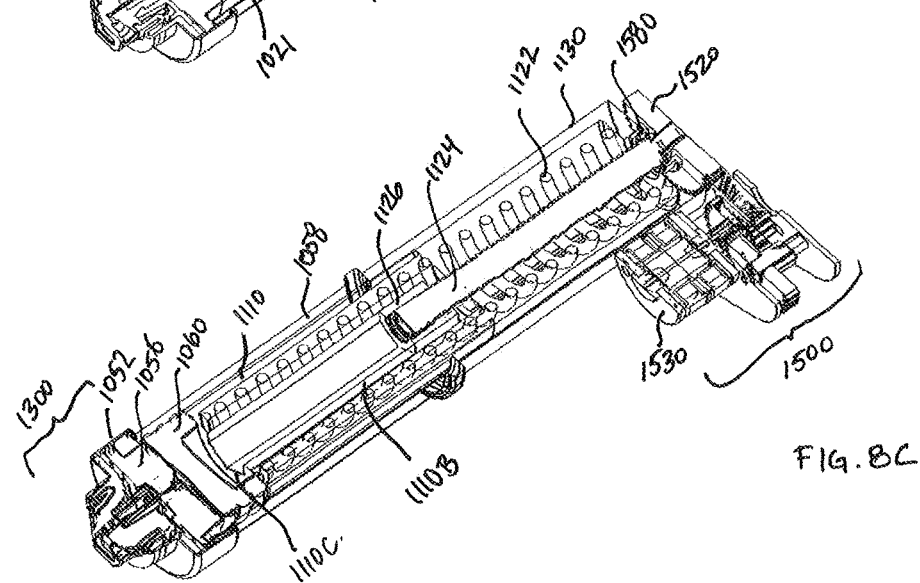
FIG. 8C shows an isometric cross-sectional view of the drive mechanism shown in FIG. 6 as the mechanism completes drug delivery.
Figure 9A:
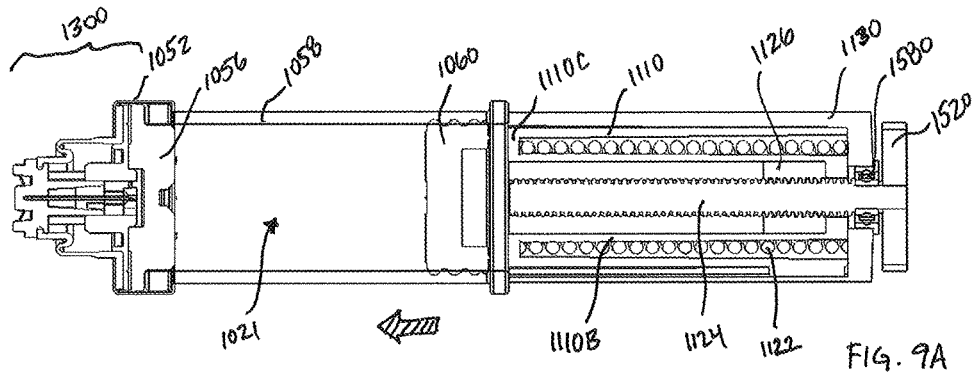
FIG. 9A shows a cross-sectional view of the drive mechanism shown in FIG. 8A in an initial inactive state.
Figure 9B:
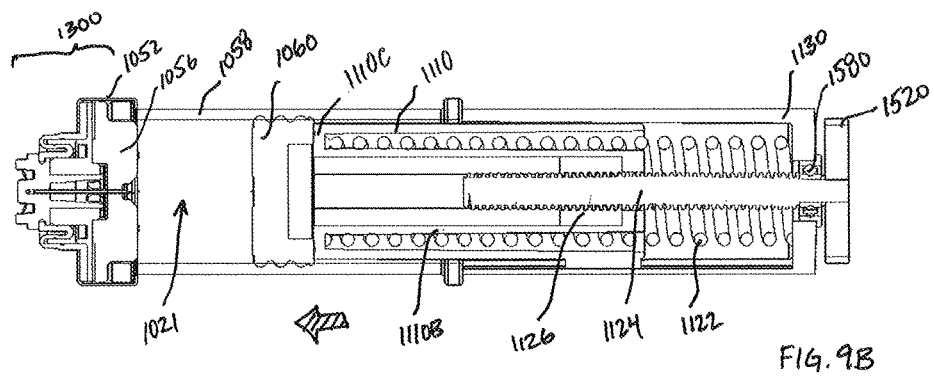
FIG. 9B shows a cross-sectional view of the drive mechanism shown in FIG. 8B in an actuated state as the mechanism controls the rate or profile of drug delivery.
Figure 9C:
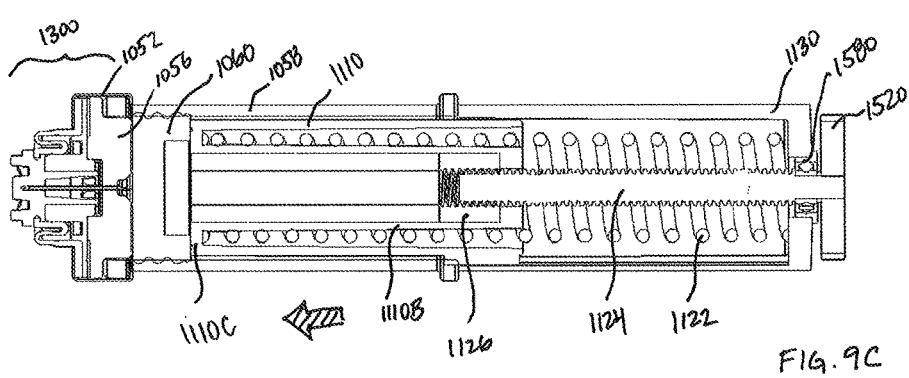
FIG. 9C shows a cross-sectional view of the drive mechanism shown in FIG. 8C as the mechanism completes drug delivery and, optionally, performs a compliance push to ensure completion of drug delivery.

FIGS. 8A-8C and FIGS. 9A-9C show the progression of the variable rate controlled delivery drive mechanism, according to the embodiment shown in FIGS. 6-7 having a non-telescoping drive mechanism configuration, as it progresses through activation, controlled delivery of a drug substance, and completion of drug delivery. As shown, a gear transmission assembly 1500 having a motor 1530 may be utilized to meter or otherwise prevent free axial translation of the biasing member 1122 used to push a plunger seal 1060 for the delivery of a drug substance out of drug chamber 1021. The gear transmission assembly 1500 is further detailed below with reference to FIGS. 10A-10B. Upon actuation of the variable rate controlled delivery drive mechanism 1100 by the user, such as by activation of the power and control system, the motor 1530 is caused to rotate the components of the gear transmission assembly 1500 to correspondingly rotate gear 1520. Substantially simultaneously or in advance of such activation of the motor 1530, the biasing member 1122 is unlocked or otherwise permitted to release from its initial energized state. The biasing member 1122 is positioned within the drive mechanism housing 1130 and held in an initial energized state between the drive mechanism housing 1130 and the interior of the interface surface 1110C of piston 1110. Upon such unlocking or release the biasing member 1122 will act upon and push the piston 1110 (and the plunger seal 1060 located substantially adjacent the piston 1110 on the other side of the interface surface 1110C) to drive the plunger seal 1060 for drug delivery, if the biasing member 1122 is unrestrained or not otherwise metered. The novel variable rate controlled delivery drive mechanisms of the present invention are configured to provide such restraint or metering on the expansion of the biasing member 1122. Depending on a desired drug delivery rate or profile, as may be pre-programmed or dynamically controlled by the power and control system, the motor 1530 of the gear assembly mechanism 1500 may function to incrementally permit axial expansion of the biasing member 1122 and, thus, axial translation of the piston 1110 and plunger seal 1060.

As the components of the gear assembly mechanism 1500 are rotated by function of the motor 1530 and corresponding gear interactions, gear 1520 is caused to rotate. A drive screw 1124 having an external pitch 1124B is connected to, or formed as part of, gear 1520. The external pitch 1124B is configured to engage and rotationally translate upon or within a nut 1126. As the gear 1520 and drive screw 1124 are axially rotated, the threaded engagement and corresponding interaction between the external pitch 1124B of the drive screw 1124 and the nut 1126 permits axial translation of the piston 1110 by the biasing member 1122. As stated above with reference to the telescoping embodiments of the present invention, the piston 1110 of the non-telescoping embodiments is rotationally keyed (i.e., constrained) to the drive housing 1130, relative to the drive screw 1124. Nut 1126 is likewise keyed to piston 1110, which configuration allows for axial translation of the piston 1110. Because the axial rotation of the drive screw 1124 directly permits axial translation of the piston 1110, such embodiments of the present invention are referred to herein as "non-telescoping". As stated above with regard to the first embodiment, the drive screw 1124, notably, does not drive the delivery but only controls the delivery motion. The drive screw 1124 controls the motion of the piston 1110 and plunger seal 1060, but does not apply the force necessary for drug delivery. Instead, the drive screw 1124 merely meters or permits translation of the piston 1110 and plunger seal 1060 which are being driven to axially translate by the biasing member 1122. Optionally, a washer or bearing 1580 may be utilized to facilitate axial rotation of gear 1520 within the drive mechanism housing 1130. Additionally, the drive mechanisms described herein may include one or more compliance features which enable additional axial translation of the plunger seal 60, 1060 to, for example, ensure that substantially the entire drug dose has been delivered to the user. For example, the plunger seal 60, 1060, itself, may have some compressibility permitting a compliance push of drug fluid from the drug container.

The novel variable rate drive mechanisms of the present invention may optionally integrate status indication into the drug dose delivery. By use of one or more status triggers and a corresponding status reader, the status of the drive mechanism before, during, and after operation can be relayed to the power and control system to provide feedback to the user. Such feedback may be tactile, visual, and/or auditory, as described above, and may be redundant such that more than one signal or type of feedback is provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. As the end-of-dose indication is tied to the piston reaching the end of its axial translation, the drive mechanism and drug pump provide a true end-of-dose indication to the user. Additionally or alternatively, an electromechanical status switch and interconnect assembly may be utilized to contact, connect, or otherwise enable a transmission to the power and control system to signal end-of-dose to the user. For example, the status switch may be located distal to the pierceable seal 56 and the interconnect located proximal to the plunger seal 60 such that, upon substantially complete axial translation (and the optional compliance push) of the plunger seal 60 within the barrel 58, the status switch and interconnect coordinate to enable a transmission to the power and control system to signal end-of-dose to the user. This configuration further enables true end-of-dose indication to the user.

FIGS. 10A and 10B shows an isometric view of certain components of a variable rate controlled delivery drive mechanism, according to at least one embodiment of the present invention. While such components are shown with reference to the embodiment detailed in FIGS. 2, 3, 4A-4C, and 5A-5C, the same or similar components may be utilized with the other embodiments of the present invention. In at least one embodiment, the gear assembly mechanism 500 of the variable rate drive mechanisms 100 of the present invention utilizes a motor 530 with pinion 530A. The pinion 530A contacts a first gear 526B of a first compound gear 526. A second gear 526A of the first compound gear 526 contacts a first gear 528B of a second compound gear 528, and a second gear 528A (not visible) of the second compound gear 528 contacts a trigger gear 524. Trigger gear 524 contacts gear 520 to relay motion to the remainder of drive mechanism 100. As the motor 530 acts upon the gear assembly mechanism 500, the motion is conveyed by interfacing gear teeth of the pinion 530A, first compound gear 526, second compound gear 528, trigger gear 524, and gear 520. As detailed above, such motion is utilized to permit, meter or otherwise restrain the axial translation of the piston 110 by the biasing member 122, thereby driving the plunger seal for drug delivery. As the trigger gear 524 rotates, a status reader 600 may read or recognize one or more corresponding status triggers on the trigger gear 524 to provide incremental status indication before, during, and after operation of the variable rate controlled delivery drive mechanism. While the drive mechanisms of the present invention are described with reference to the gear assembly mechanism shown in FIGS. 10A and 10B, a range of gear assembly configurations with the appropriate gear reduction based on the load and motor chosen would be acceptable and capable of being employed within the embodiments of the present invention, as would readily be appreciated by an ordinarily skilled artisan. Accordingly, the embodiments of the present invention are not limited to the specific gear assembly mechanism described herein, which is provided as an exemplary embodiment of such mechanisms for employment within controlled delivery drive mechanisms and drug delivery pumps.

As described above, a number of status readers may be utilized within the embodiments of the present invention. For example, the drive mechanism shown in FIG. 10A may utilize a mechanical status reader 600 which is physically contacted by gear teeth of the trigger gear 524. As the status reader 600 is contacted by the status trigger(s), which in this exemplary embodiment are the gear teeth of the trigger gear 524, the status reader 600 measures the rotational position of the trigger gear 524 and transmits a signal to the power and control system for status indication to the user. Additionally or alternatively, as shown in FIG. 10B, the drive mechanism may utilize an optical status reader 1600. The optical status reader 1600 may be, for example, a light beam that is capable of recognizing a motion and transmitting a signal to the power and control system. For example, the drive mechanism shown in FIG. 10B may utilize an optical status reader 1600 that is configured to recognize motion of the gear teeth of the trigger gear 524. As would be appreciated by one having ordinary skill in the art, optical status readers and corresponding triggers, electromechanical status readers and corresponding triggers, and/or mechanical status readers and corresponding triggers may all be utilized by the embodiments of the present invention to provide incremental status indication to the user.

Returning now to the embodiments shown in FIGS. 2-3 and FIGS. 6-7, a fluid, such as a drug fluid, may be contained within barrel 58, 1058, in a drug chamber 21, 1021 between plunger seal 60, 1060 and pierceable seal 56, 1056, for delivery to a user. The pierceable seal is adjacent or retained at least partially within cap 52, 1052. Upon activation by the user, a fluid pathway connection may be connected to the drug container through the pierceable seal. As described above, this fluid connection may be facilitated by a piercing member of the fluid pathway connection which pierces the pierceable seal and completes the fluid pathway from the drug container, through the fluid pathway connection, the fluid conduit, the insertion mechanism, and the cannula for delivery of the drug fluid to the body of the user. Initially, one or more locking mechanisms (not shown) may retain the biasing member 122, 1122 in an initial energized position within piston 110, 1110. Directly or indirectly upon activation of the device by the user, the locking mechanism may be removed to permit operation of the drive mechanism. The piston 110, 1110 and biasing member 122, 1122 are both initially in a compressed, energized state behind (i.e., proximal to) the plunger seal 60, 1060. The biasing member 122, 1122 may be maintained in this state until activation of the device between internal features of drive housing 130, 1130 and interface surface 110C, 1110C of piston 110, 1110. As the locking mechanism is removed or displaced, biasing member 122, 1122 is permitted to expand (i.e., decompress) axially in the distal direction (i.e., in the direction of the hatched arrow). Such expansion causes the biasing member 122, 1122 to act upon and distally translate interface surface 110C, 1110C and piston 110, 1110, thereby distally translating plunger seal 60, 1060 to push drug fluid out of the drug chamber 21, 1021 of barrel 58, 1058. Distal translation of the piston 110, 1110 and plunger seal 60, 1060 continues to force fluid flow out from barrel 58, 1058 through pierceable seal 56, 1056. In at least one embodiment, an end-of-dose status indication may be provided to the user once the status reader recognizes a status trigger positioned on the trigger gear to substantially correspond with the end of axial travel of the piston 110, 1110 and plunger 60, 1060. The gear assembly mechanism 500, 1500 and novel drive mechanisms 100, 1100 of the present invention thus permit, meter, or otherwise restrain the free axial expansion of the biasing member 122, 1122 to control the rate or profile of drug delivery. The novel embodiments of the present invention also thus provide incremental status indication to the user.

Assembly and/or manufacturing of variable rate controlled delivery drive mechanism 100, 1100, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 50 may first be assembled and filled with a fluid for delivery to the user. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 may guide the insertion of the piercing member of the fluid pathway connection into the barrel 58 of the drug container 50. The drug container 50 may then be mounted to a distal end of drive housing 130.

A drive biasing member 122 may be inserted into a distal end of the drive housing 130. Optionally, a cover sleeve 140 may be inserted into a distal end of the drive housing 130 to substantially cover biasing member 122. A piston may be inserted into the distal end of the drive housing 130 such that it resides at least partially within an axial pass-through of the biasing member 122 and the biasing member 122 is permitted to contact a piston interface surface 110C of piston 110 at the distal end of the biasing member 122. The piston 110 and drive biasing member 122, and optional cover sleeve 140, may be compressed into drive housing 130. Such assembly positions the drive biasing member 122 in an initial compressed, energized state and preferably places a piston interface surface 110C in contact with the proximal surface of the plunger seal 60 within the proximal end of barrel 58. The piston, piston biasing member, contact sleeve, and optional components, may be compressed and locked into the ready-to-actuate state within the drive housing 130 prior to attachment or mounting of the drug container 50. The drive screw 1124, or combination of first screw 124 and second screw 132, and their corresponding engagement components may be pre-assembled, connected to the piston 110, mounted into the drive mechanism housing 130 and connected to gear drive 120 and gear 520 (or alternatively connected to gear 1520) which is placed in position through the proximal end of the drive mechanism housing 130 such that it extends proximally therefrom to engage the gear assembly mechanism 500, 1500 for operation.

A fluid pathway connection, and specifically a sterile sleeve of the fluid pathway connection, may be connected to the cap and/or pierceable seal of the drug container. A fluid conduit may be connected to the other end of the fluid pathway connection which itself is connected to the insertion mechanism such that the fluid pathway, when opened, connected, or otherwise enabled travels directly from the drug container, fluid pathway connection, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug pump, as shown in FIG. 1B.

Certain optional standard components or variations of drive mechanism 100, drive mechanism 1100, or drug pump 10 are contemplated while remaining within the breadth and scope of the present invention. For example, the embodiments may include one or more batteries utilized to power the motor, drive mechanisms, and drug pumps of the present invention. A range of batteries known in the art may be utilized for this purpose. Additionally, upper or lower housings may optionally contain one or more transparent or translucent windows 18, as shown in FIG. 1A, to enable the user to view the operation of the drug pump 10 or verify that drug dose has completed. Similarly, the drug pump 10 may contain an adhesive patch 26 and a patch liner 28 on the bottom surface of the housing 12. The adhesive patch 26 may be utilized to adhere the drug pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug pump 10 in contact with the body of the user. Removal of the patch liner 28 may further remove the sealing membrane 254 of the insertion mechanism 200, opening the insertion mechanism to the body of the user for drug delivery (as shown in FIG. 1C).

Similarly, one or more of the components of variable rate controlled delivery drive mechanism 100, drive mechanism 1100, and drug pump 10 may be modified while remaining functionally within the breadth and scope of the present invention. For example, as described above, while the housing of drug pump 10 is shown as two separate components upper housing 12A and lower housing 12B, these components may be a single unified component. As discussed above, a glue, adhesive, or other known materials or methods may be utilized to affix one or more components of the variable rate controlled delivery drive mechanism and/or drug pump to each other. Alternatively, one or more components of the variable rate controlled delivery drive mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the variable rate drive mechanisms and drug pumps disclosed herein provide an efficient and easily-operated system for automated drug delivery from a drug container. The novel embodiments described herein provide drive mechanisms for the controlled delivery of drug substances and drug delivery pumps which incorporate such variable rate drive mechanisms. The drive mechanisms of the present invention control the rate of drug delivery by metering, providing resistance, or otherwise preventing free axial translation of the plunger seal utilized to force a drug substance out of a drug container and, thus, are capable of delivering drug substances at variable rates and/or delivery profiles. Additionally, the drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. The novel variable rate drive mechanisms of the present invention may be directly or indirectly activated by the user. Furthermore, the novel configurations of the variable rate controlled delivery drive mechanism and drug pumps of the present invention maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly.

Manufacturing of a drug pump includes the step of attaching both the variable rate controlled delivery drive mechanism and drug container, either separately or as a combined component, to an assembly platform or housing of the drug pump. The method of manufacturing further includes attachment of the fluid pathway connection, drug container, and insertion mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the drug pump includes the steps of: activating, by a user, the activation mechanism; displacing a control arm to actuate an insertion mechanism; and actuating a power and control system to activate a variable rate controlled delivery drive mechanism to drive fluid drug flow through the drug pump according to a controlled rate or drug delivery profile. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the variable rate controlled delivery drive mechanism by the expansion of the biasing member acting upon a piston within a drug container to force fluid drug flow through the drug container, the fluid pathway connection, a sterile fluid conduit, and the insertion mechanism for delivery of the fluid drug to the body of a user, wherein a drive gear or screw acting on the piston is utilized to restrain the free axial translation of the piston. The method of operation of the insertion mechanism and the drug pump may be better appreciated with reference to FIGS. 4A-4C, FIGS. 5A-5C, FIGS. 8A-8C, and FIGS. 9A-9C, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A variable rate controlled delivery drive mechanism comprising: a drive mechanism housing, a biasing member positioned in an initially energized state within an inner cavity of a piston; a gear drive having a gear and a substantially axial internal pass-through; a first screw at least partially residing within the axial internal pass-through, said first screw also having a substantially axial pass-through and an external first pitch wherein the external first pitch is configured to engage a first nut residing within the axial internal pass-through of the gear drive; a second nut configured to engage a second screw having an external second pitch, said second nut positioned within an axial post of a piston, said axial post and second nut positioned to reside at least partially within the axial pass-through of the first screw; wherein the piston has an interface surface adjacent to a plunger seal and is configured to axially translate the plunger seal, by force asserted upon it from the biasing member, from a first position to a second position within a drug container for drug delivery, and wherein the biasing member is metered from free expansion from its energized state.

2. The drive mechanism of claim 1, wherein the drug container contains a drug fluid within a drug chamber.

3. The drive mechanism of claim 1, wherein a cover sleeve is configured to engage and slide upon the piston, between the piston and a distal end of the drive mechanism housing.

4. The drive mechanism of claim 1, wherein the first nut is rotationally constrained to the gear drive.

5. The drive mechanism of claim 1, wherein the second nut is rotationally constrained to the piston.

6. The drive mechanism of claim 1 further comprising a gear assembly mechanism having a motor, the gear assembly mechanism configured to engage the gear to meter the free expansion of the biasing member from its energized state.

7. The drive mechanism of claim 6, wherein the gear assembly mechanism having the motor further comprises a pinion extending from the motor; a first compound gear having a first gear and a second gear; a second compound gear having a first gear and a second gear; and a trigger gear; wherein the pinion contacts the first gear of the first compound gear, the second gear of the first compound gear contacts the first gear of the second compound gear, the second gear of the second compound gear contacts the trigger gear, and the trigger gear contacts the gear to relay motion to the drive mechanism.

8. The drive mechanism of claim 6, wherein the metering of the biasing member controls a rate or profile of drug delivery to a user.

9. The drive mechanism of claim 1, further comprising a status reader configured to read or recognize one or more corresponding status triggers, wherein, during operation of the drive mechanism, interaction between the status reader and the one or more status triggers is configured to transmit a signal to a power and control system to provide feedback to a user.

10. The drive mechanism of claim 9, wherein the status reader is an optical status reader and the one or more corresponding status triggers are gear teeth of a trigger gear.

11. The drive mechanism of claim 9, wherein the status reader is a mechanical status reader and the one or more corresponding status triggers are gear teeth of a trigger gear.

12. The drive mechanism of claim 9, wherein the status reader is a mechanical status reader and the one or more corresponding status triggers are external features of the piston and/or a cover sleeve.

13. The drive mechanism of claim 9, wherein the status reader is an optical status reader and the one or more corresponding status triggers are external features of the piston and/or a cover sleeve.

14. The drive mechanism of claim 6, wherein a function of the gear assembly mechanism having the motor is pre-programmed or dynamically controlled by a power and control system to meet a desired drug delivery rate or profile.

15. A drug delivery pump comprising: a drug delivery pump housing; an activation mechanism; an insertion mechanism; a fluid pathway connection; a power and control system; and a variable rate controlled delivery drive mechanism having a drug container, and a drive mechanism comprising a drive mechanism housing, a biasing member positioned in an initially energized state within an inner cavity of a piston; a gear drive having a gear and a substantially axial internal pass-through; a first screw which at least partially resides within the axial internal pass-through, said first screw also having a substantially axial pass-through and an external first pitch wherein the external first pitch is configured to engage a first nut which also resides within the internal pass-through of the gear drive; a second nut configured to engage a second screw having an external second pitch, said second nut positioned within an axial post of a piston, said axial post and second nut positioned to reside at least partially within the axial pass-through of the first screw; wherein the piston has an interface surface adjacent to a plunger seal and is configured to axially translate the plunger seal, by force asserted upon it from the biasing member, from a first position to a second position within the drug container for drug delivery, and wherein the biasing member is metered from free expansion from its energized state.

16. The drug delivery pump of claim 15, wherein the drug container contains a drug fluid within a drug chamber.

17. The drug delivery pump of claim 15, further comprising a gear assembly mechanism having a motor, the gear assembly mechanism configured to engage the gear to meter the free expansion of the biasing member from is energized state.

18. The drug delivery pump of claim 17, wherein the gear assembly mechanism further comprises a pinion extending from the motor; a first compound gear having a first gear and a second gear; a second compound gear having a first gear and a second gear; and a trigger gear; wherein the pinion contacts the first gear of the first compound gear, the second gear of the first compound gear contacts the first gear of the second compound gear, the second gear of the second compound gear contacts the trigger gear, and the trigger gear contacts the gear to relay motion to the drive mechanism.

19. The drug delivery pump of claim 17, wherein a function of the gear assembly mechanism having the motor is pre-programmed or dynamically controlled by the power and control system to meet a desired drug delivery rate or profile.

20. The drug delivery pump of claim 17, wherein a metering of the biasing member controls a rate or profile of drug delivery to a user.

21. The drug delivery pump of claim 15, further comprising a status reader configured to read or recognize one or more corresponding status triggers, wherein, during operation of the drive mechanism, interaction between the status reader and the one or more status triggers is configured to transmit a signal to the power and control system to provide feedback to a user.

22. The drug delivery pump of claim 21, wherein the status reader is an optical status reader and the one or more corresponding status triggers are gear teeth of a trigger gear.

23. The drug delivery pump of claim 21, wherein the status reader is a mechanical status reader and the one or more corresponding status triggers are gear teeth of a trigger gear.

24. The drug delivery pump of claim 21, wherein the status reader is a mechanical status reader and the one or more corresponding status triggers are external features of the piston and/or a cover sleeve.

25. The drug delivery pump of claim 21, wherein the status reader is an optical status reader and the corresponding status triggers are external features of the piston and/or a cover sleeve.

* * * * *

UNITED STATES PATENT AND TRADEMARK OFFICE
CERTIFICATE OF CORRECTION

PATENT NO. : 10,251,996 B2
APPLICATION NO. : 14/423565
DATED : April 9, 2019
INVENTOR(S) : Paul F. Bente, IV et al.

Page 1 of 1

It is certified that error appears in the above-identified patent and that said Letters Patent is hereby corrected as shown below:

In the Claims

In Column 25, Claim 17, Line 24, please delete "is" and insert -- it's --.

Signed and Sealed this
Eighteenth Day of June, 2019

Andrei Iancu
*Director of the United States Patent and Trademark Office*